(12) United States Patent
Singh et al.

(10) Patent No.: US 6,403,807 B1
(45) Date of Patent: Jun. 11, 2002

(54) BRIDGED FLUORESCENT DYES, THEIR PREPARATION AND THEIR USE IN ASSAYS

(75) Inventors: Rajendra Singh, San Jose, CA (US); Gregory Gorski, Bryn Mawr, PA (US); Gary Frenzel, Mountain View, CA (US)

(73) Assignee: SurroMed, Inc., Mountain View, CA (US)

( * ) Notice: Subject to any disclaimer, the term of this patent is extended or adjusted under 35 U.S.C. 154(b) by 0 days.

(21) Appl. No.: 09/612,331

(22) Filed: Jul. 6, 2000

Related U.S. Application Data

(60) Provisional application No. 60/142,477, filed on Jul. 6, 1999.

(51) Int. Cl.[7] .................... C07D 403/06; C07D 403/08; C07D 417/06; C07D 417/08; C07D 413/06
(52) U.S. Cl. .................... 548/455; 436/546; 530/391.3; 530/402; 548/100; 548/156; 548/219; 548/305.4; 548/305.7
(58) Field of Search .................... 436/546; 435/188; 530/391.3, 402; 548/156, 219, 305.4, 305.7, 455, 100

(56) References Cited

U.S. PATENT DOCUMENTS

| | | |
|---|---|---|
| 3,817,837 A | 6/1974 | Rubenstein et al. |
| 3,821,233 A | 6/1974 | Lincoln et al. |
| 3,864,644 A | 2/1975 | Lincoln et al. |
| 3,904,637 A | 9/1975 | Lincoln et al. |
| 3,996,345 A | 12/1976 | Ullman et al. |
| 3,998,943 A | 12/1976 | Ullman |
| 4,011,086 A | 3/1977 | Simson |
| 4,233,402 A | 11/1980 | Maggio et al. |
| 4,256,834 A | 3/1981 | Zuk et al. |
| 4,261,968 A | 4/1981 | Ullman et al. |
| 4,275,149 A | 6/1981 | Litman et al. |
| 4,490,463 A | 12/1984 | Gilbert |
| 4,806,488 A | 2/1989 | Berger, Jr. et al. |
| 4,830,786 A | 5/1989 | Pease et al. |
| 5,039,818 A | 8/1991 | Pease et al. |
| 5,268,486 A | 12/1993 | Waggoner et al. |
| 5,310,922 A | 5/1994 | Pease et al. |
| 5,329,019 A | 7/1994 | Pease et al. |
| 5,416,214 A | 5/1995 | Pease et al. |
| 5,486,616 A | 1/1996 | Waggoner et al. |
| 5,569,587 A | 10/1996 | Waggoner |
| 5,569,766 A | 10/1996 | Waggoner et al. |
| 5,571,388 A | 11/1996 | Patonay et al. |
| 5,627,027 A | 5/1997 | Waggoner |
| 5,800,995 A | 9/1998 | Patonay et al. |
| 6,133,445 A | * 10/2000 | Waggoner et al. |

FOREIGN PATENT DOCUMENTS

| | | |
|---|---|---|
| EP | 0 670 374 A1 | 9/1995 |
| EP | 0 747 448 A2 | 12/1996 |
| EP | 1 042 407 B1 | * 12/1998 |
| WO | WO 97/40104 | 10/1997 |

OTHER PUBLICATIONS

Schmidt et al., Chemical Abstracts No. 90: 78823 (1979).*
Ibraev et al., Chemical Abstracts No. 127: 363715 (1997).*
Balog et al., Chemical Abstracts No. 120: 152594 (1994).*
Chibisov et al. (1995) J. Phys. Chem. 99:886.
Mushkalo et al. A Macrocyclic Bis–Cyanine Dye. Tetrahedron Letters. 1980. 21, 2977–2980.
Chibisov et al. Photorelaxation Processes in Covalently Linked Indocarbocyanine and Thiacarbocyanine Dyes. Journal of Physical Chemistry. 1995. 99, 886–893.

* cited by examiner

*Primary Examiner*—Mary E. Ceperley
(74) *Attorney, Agent, or Firm*—Swanson & Bratschun, L.L.C.

(57) ABSTRACT

Bridged fluorescent dyes of the cyanine and squaraine families are disclosed. The dyes are useful as markers in assay techniques and offer advantages of undergoing excitation at a common wavelength but emitting at structure dependent different wavelengths.

20 Claims, 19 Drawing Sheets

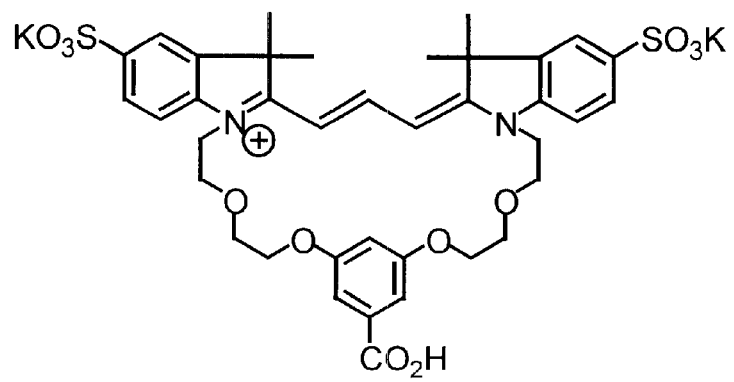
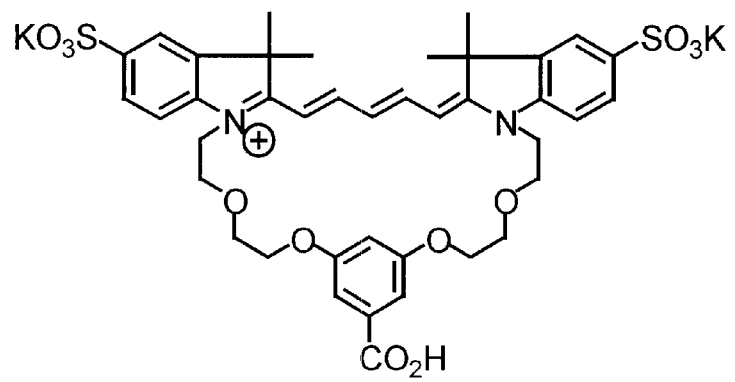
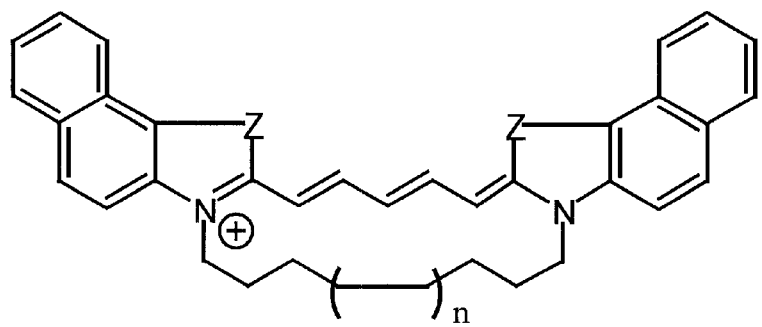
n = 1-6;
Z = C(Me)2, O, S, Se or N
Fig. 2 (Page 1)

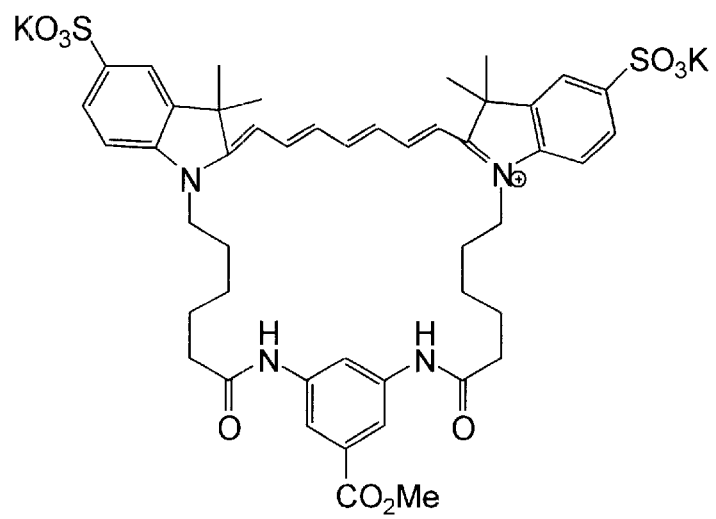
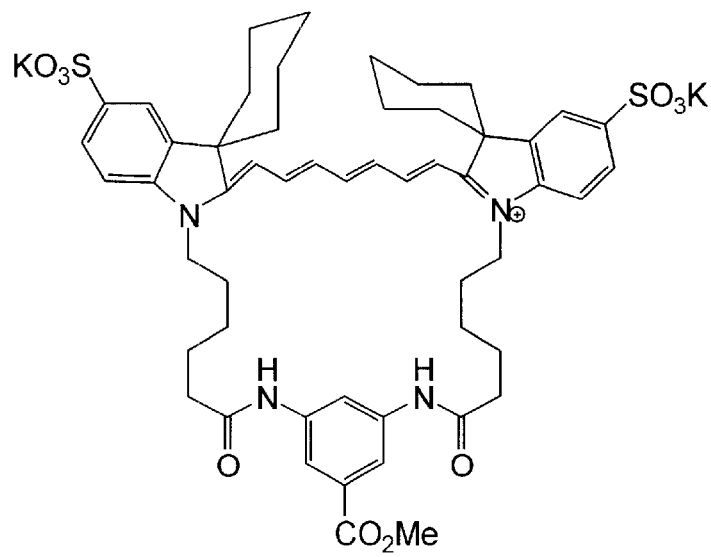
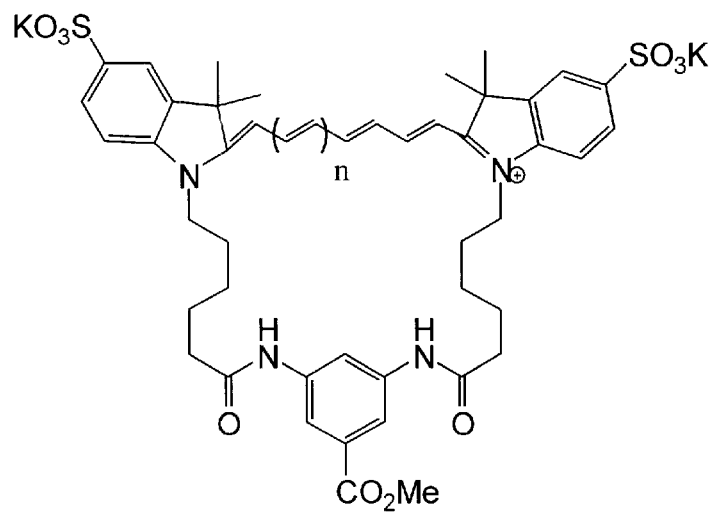
Fig. 2 (Page 2)

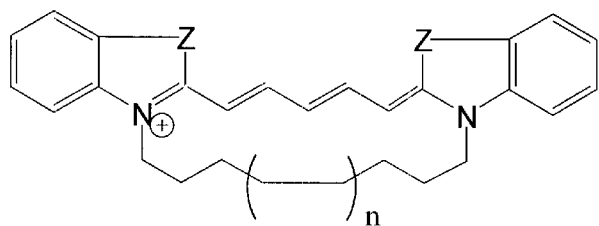
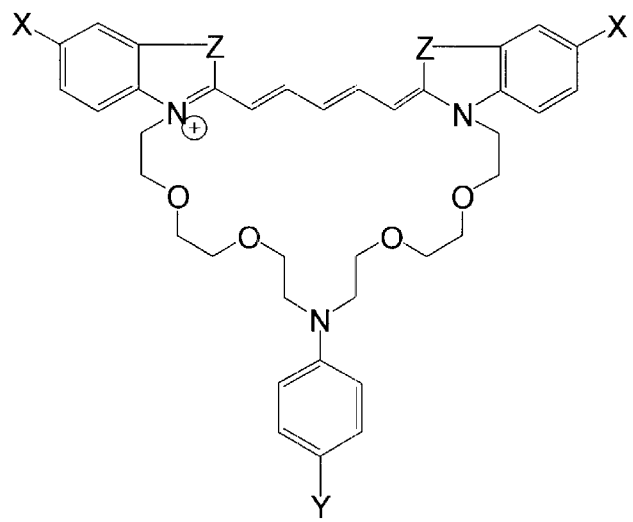
n = 1-6
X = OPO$_3$M$_2$, PO$_3$M$_2$, B(OH)$_2$
Y = 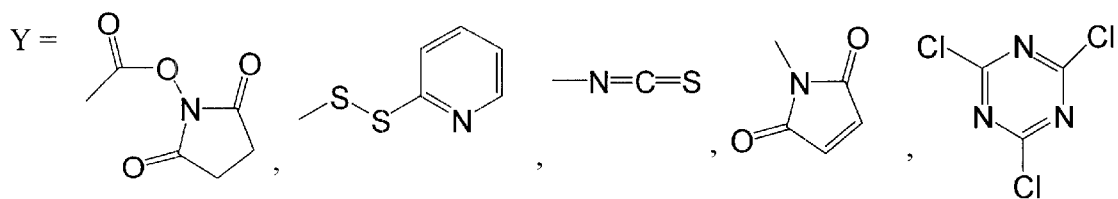
Z = C(Me)$_2$, O, S, Se or N
Fig. 2 (Page 3)

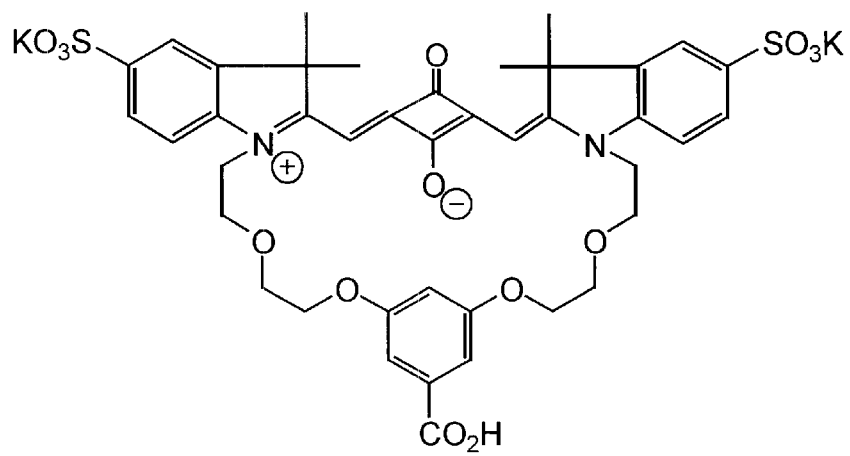
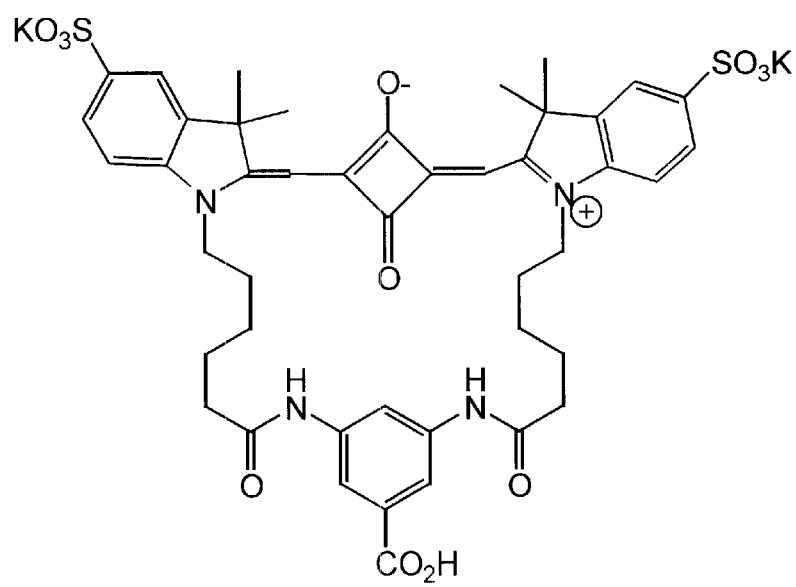
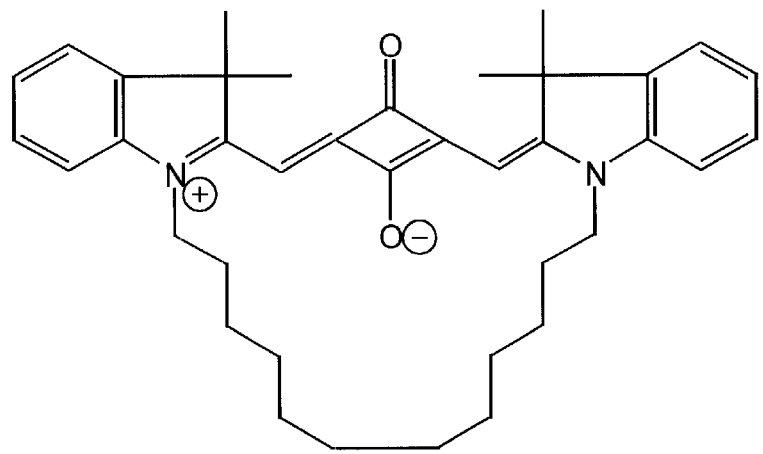
Fig. 2 (Page 4)

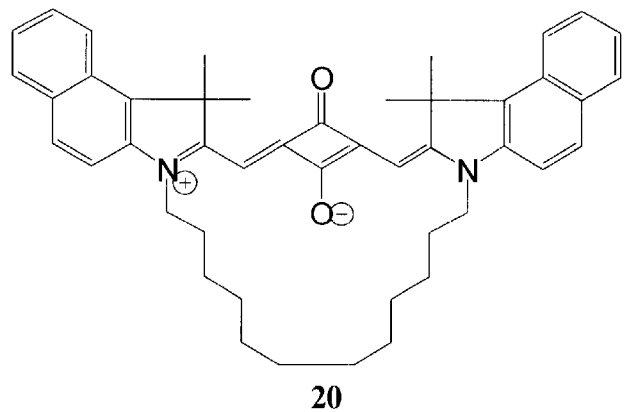
20
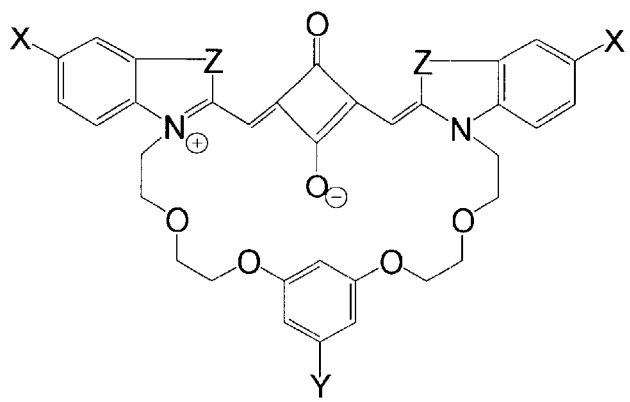
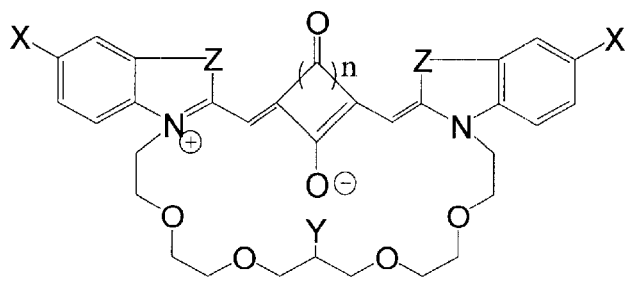
n = 1, 2, 3
X = OPO$_3$M$_2$, PO$_3$M$_2$, B(OH)$_2$
Y = 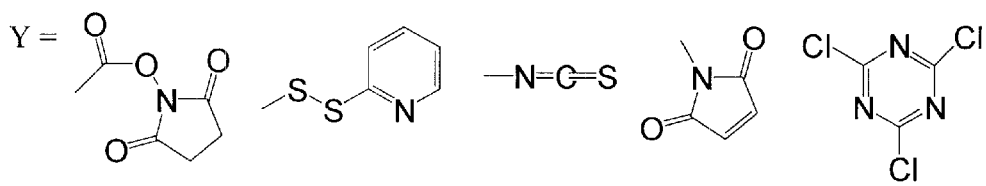
Z = C(Me)$_2$, O, S, Se or N
Fig. 2 (Page 5)

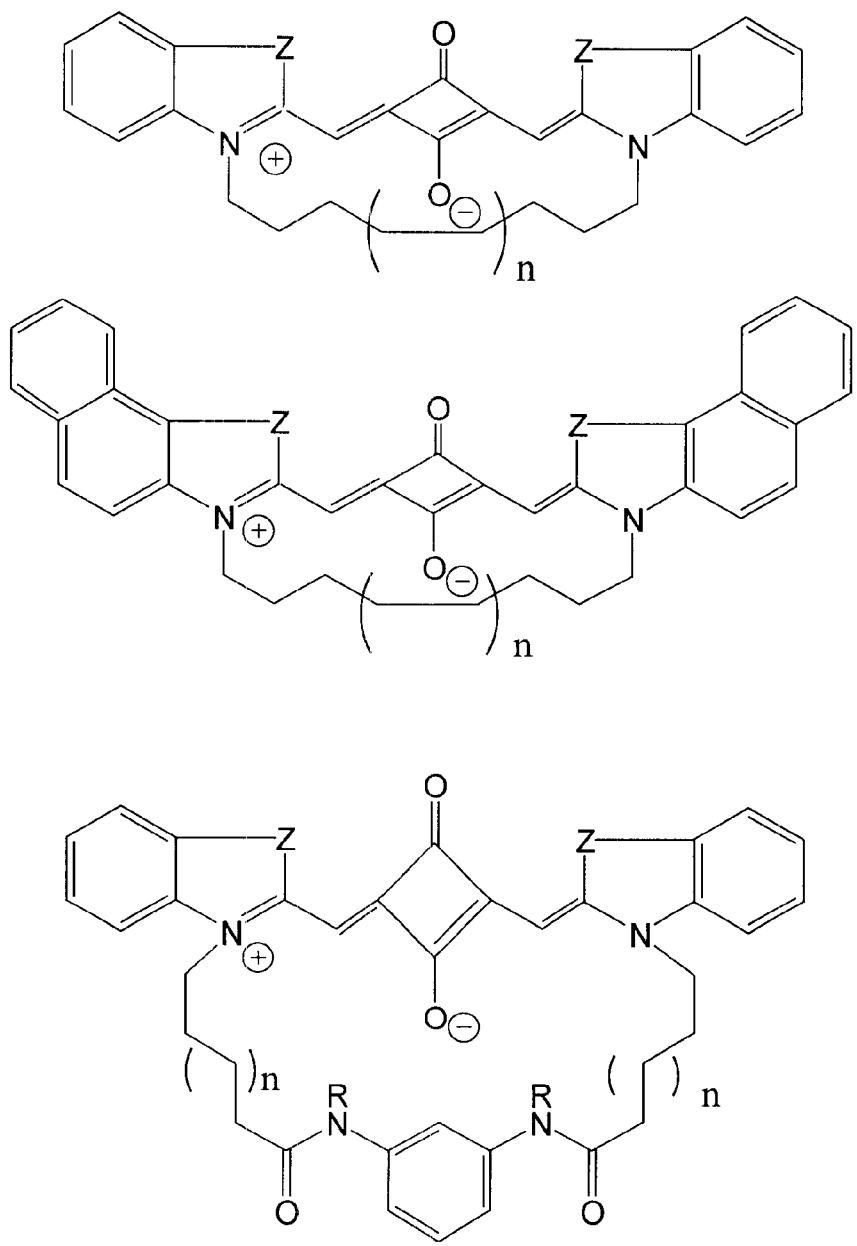
n = 1 to 6
Z = (CMe)$_2$, O, S, Se or N
R = H or alkyl
Fig. 2 (Page 6)

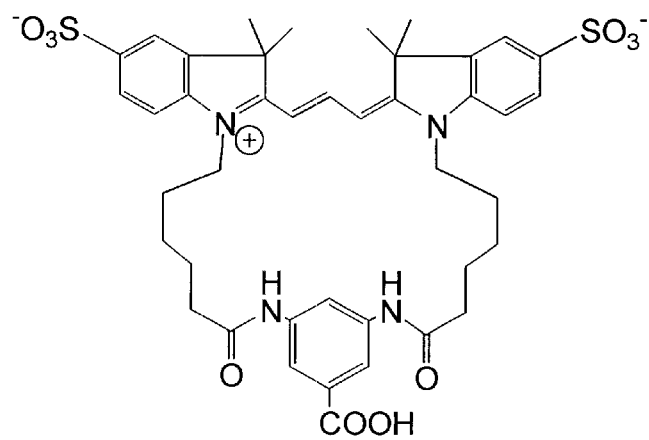
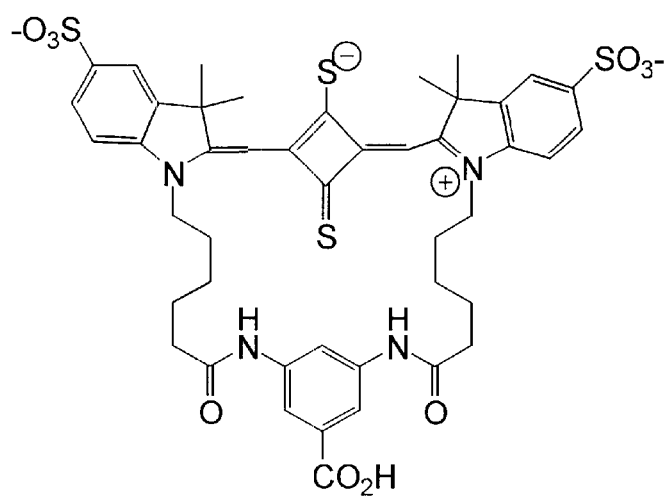
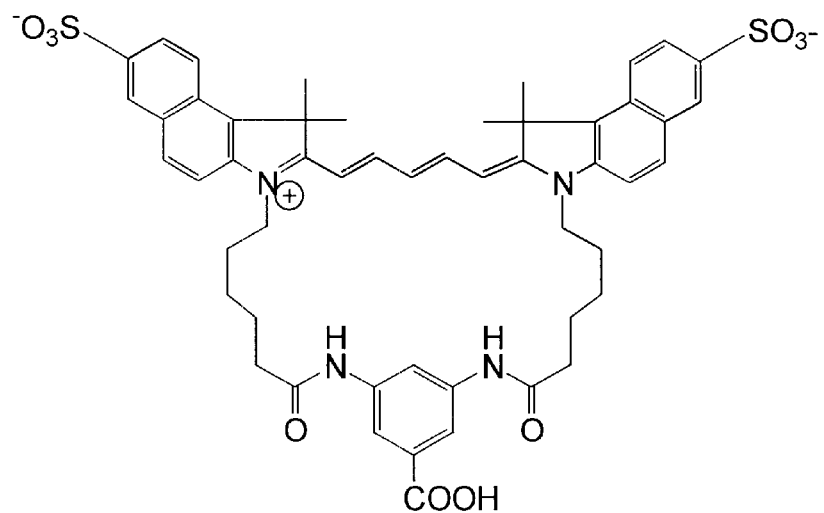
Fig. 2 (Page 7)

US 6,403,807 B1

BRIDGED FLUORESCENT DYES, THEIR PREPARATION AND THEIR USE IN ASSAYS

RELATED APPLICATIONS

This application claims priority from U.S. Provisional Application Serial No. 60/142,477, filed Jul. 6, 1999, entitled "Bridged Fluorescent Dyes, Their Preparation and Their Use in Assays."

FIELD OF INVENTION

This invention relates to fluorescent compounds, their preparation and their use as labels in assay techniques.

BACKGROUND OF THE INVENTION

Fluorescent compounds find wide application because of their ability to emit light upon excitation with energy within certain energy ranges. By virtue of this ability, fluorophores have found employment as labels in chemical or biological processes, e.g., assays. That is, various compounds can be conjugated to a fluorescent compound, the conjugate subjected to some type of partitioning, and the fate of the conjugate determined by irradiating the sample with light and detecting the zone in which the conjugate exists.

This technique can be employed, for example, in immunoassays involving specific binding pairs, such as DNA and like genomic material, ligands and receptors, e.g., antigens and antibodies. By conjugating a fluorophore to one of the members of the specific binding pair and employing various protocols, one can provide for partitioning of the fluorophore conjugate between a solid phase and a liquid phase in relation to the amount of antigen in an unknown sample. By measuring the fluorescence of either of the phases, one can then relate the level of fluorescence observed to a concentration of the antigen in the sample.

Alternatively, one can avoid partitioning of the fluorescent label by providing for a mechanism that varies the fluorescence of the label, depending upon the label environment in a liquid medium.

There is a particular interest in fluorescent compounds and assay techniques that permit multiple species to be labeled with different fluorophores. It is advantageous if the different fluorophores emit at distinguishably different wavelengths. It is also advantageous if the different fluorophores can be excited at a single wavelength. It is further desired to have fluorophores which are constructed to be chemically stable and to maintain their fluorescent conformation during use.

Photophysical characteristics of fluorophores play an important role in biological systems utilizing fluorescence detection techniques. The photographic industry has provided a number of fluorescent dyes with excellent photochemical properties in the form of high extinction coefficients, quantum yields and photostability. The cyanine, phthalocyanine, naphthalocyanine and squaraine classes of dyes have been used as sensitizers for photography and xerography in addition to being used as laser dyes, dyes for polymers, analytical indicators and fluorescent markers for biological macromolecules.

These commercially available dyes are typically hydrophobic and have to be dissolved in organic solvents prior to covalent attachment to proteins or nucleic acids which are usually in an aqueous media. This is a limitation to their use as fluorescent labeling reagents, as the requirement for an organic solvent or mixed solvent systems in which the biological macromolecules are only marginally soluble may result in poor labeling. Additionally, the organic solvents may be deleterious to the macromolecules. Post labeling, these hydrophobic dyes tend to π stack in an aqueous environment which leads to fluorescence quenching. These hydrophobic dyes also bind nonspecifically to macromolecules by van der Waals and dipole-dipole type interactions. Such noncovalent attachment leads to instability and lower signal/noise ratio in assays employing these reagents.

The arylsulfonate cyanine dyes developed by Waggoner et al. (U.S. Pat. Nos. 5,569,766; 5,486,616; 5,268,486; 5,569,587 and 5,627,027) provide higher levels of solubility in aqueous media than similar hydrophobic materials. These dyes, with their sulfonate groups are also less prone to hydrophobic interactions such as stacking interactions when covalently bound to macromolecules. The latter effect leads to higher quantum yields in aqueous media and translates to a brighter labeling reagent, an important criteria for sensitive detection methods that use fluorescence. These arylsulfonate cyanine dyes also have functional groups appended to them for covalently coupling to macromolecules. Their absorption wavelength can be tailored to match existing instrumentation, which in turn increases their potential to be used as fluorophores for multiparameter analysis in cytometry and diagnostics.

Cyanine dyes have two heterocyclic moieties (typically two of the same heterocyclic moiety) covalently linked by a conjugated, unsaturated bridge. The extent of conjugation, the length of the linking chain and the nature of the heterocyclic groups determines the absorption wavelength.

The squaraine and the croconine dyes present a similar overall structure with the same types of heterocyclic groups linked through a conjugated, unsaturated chain. In the case of these materials, the linking chain includes an intervening cyclobuteneolate or cyclopenteneolate moiety.

The functional groups for linking these dyes to proteins are usually appended to the heterocyclic moiety by an appropriate linker. Two representative synthetic routes described in the art for forming these dyes and incorporating linking groups are provided in FIG. 1. Both routes go through a common intermediate, compound 3, which provides the heterocyclic moiety. In the case of the shorter route, 3 to 5 to 7, two molecules of 3 are linked to opposite ends of a precursor to the conjugated bridge. The presence of two heterocycles in each dye molecule prepared by this route therefore leads to a bisfunctional derivative such as the Cy7 bis-N-hydroxy succinimide ester 7, shown in FIG. 1. The bisfunctional derivatives provided by this synthetic route could cause the proteins to crosslink and in case of certain antibodies compromise their binding capacity. An alternative synthetic route, 3 to 4 to 6 to 8, is also shown in FIG. 1. This route employs a stepwise condensation of a functional-group-bearing heterocycle with an appropriate aldehyde. While it does yield the monofunctional derivative (as exemplified by the Cy5 mono N-hydroxy succinimide ester 6 synthesized in FIG. 1), the isolation and purification of intermediate 4, is problematic as some symmetrical (bisfunctional) dye is invariably produced. The length of the synthesis (five steps for monofunctional material versus three steps for bisfunctional), plus the tedious purification involved highlight the need for alternative methods for the synthesis of monofunctional cyanine and squaraine dyes that would be easier to carry out and would yield products that would be consequently easier to purify, as provided by the present invention.

The fluorescent dyes provided by the present invention include a second covalent link bridging the two heterocycles and restraining their motion relative to one another into conformations which favor fluorescent emission at wavelengths that are advantageous for use in assays. Other bridged cyanine dyes have been described in U.S. Pat. Nos. 5,571,388; 5,800,995; 4011,086; 3,904,637; 3,864,644; 3,821,233 and 4,490,463. Those in U.S. Pat. Nos. 5,571,388 and 5,800,995 have absorption and emission in the near to far infra red regions of the spectrum and lack functional groups necessary for water solubility. The materials shown in the earlier patents have rigidized monomethine or trimethine moieties linking the heterocycles. These materials absorb at lower wavelengths and also lack functional groups necessary for aqueous solubility, as well as, attachment to macromolecules.

A group of squaraine dyes have been described in U.S. Pat. No. 4,830,786 and subsequent divisional patents, U.S. Pat. Nos. 5,329,019; 5,416,214; 5,310,922 and 5,039,818. Assays for ligands and receptors employing conjugates of these dyes have been described in U.S. Pat. No. 4,806,488. Squaraine dyes with detergent-like properties have been used to stain cells in whole blood for the determination of blood group antigens. Squaraine dyes have also been used in fluorescent nucleic acid sequencing as described in WO 97/40104. Bridged squaraine dyes linked through nitrogens in the heterocyclic units are not known.

SUMMARY OF THE INVENTION

The present invention provides novel compounds in the squaraine and cyanine dye families. Squaraine and cyanine dyes share a common structure having two heterocyclic units conjugated to one another through an unsaturated linking chain. The compounds of the present invention are characterized by having a separate second linking chain joining the two heterocycles to restrain the compound into a desired conformation which absorbs electromagnetic energy at wavelengths greater than about 500 nm and especially greater than about 600 nm and emits fluorescence at wavelengths in the range of from about 640 nm to about 840 nm. This makes the compounds particularly suitable for excitation at such wavelengths such as the 633 nm wavelength of a helium/neon laser. A range of materials having a variety of fluorescence wavelengths are achieved.

In certain embodiments these compounds include one or more hydrophilic groups present to enhance water solubility. In other embodiments, they can be relatively oleophilic. Also, these compounds can include groups to facilitate their covalent attachment to proteins, nucleic acids and other biological and non-biological materials to make these materials fluoresce so that they can be detected in assays.

In another embodiment, this invention provides an improved method for preparing the bridged cyanine and squaraine dyes. In accord with this method, the two heterocycles present in both of these types of dyes are assembled prior to condensation with the conjugated unsaturated bridge by linking them together using an appropriate "second" bridge which does not impart conjugation to the overall dye molecule and which may carry a functional group. This strategy yields monofunctional derivatives. Additionally, the facile intramolecular condensation involved in forming the dyes is an advantage over the less favorable intermolecular approach usually used.

In other embodiments, this invention provides the labeled materials which result when the dyes are attached to biological materials, methods of labeling and methods of analysis employing the labeled materials.

It is to be understood that both the foregoing general description and the following detailed description are exemplary and explanatory only and are not restrictive of the invention as claimed.

BRIEF DESCRIPTION OF THE DRAWINGS

The invention will be further described with reference being made to the accompanying drawings in which:

FIG. 2 is a series of chemical formulae depicting representative dyes of this invention.

DETAILED DESCRIPTION OF THE INVENTION

Figure 1:
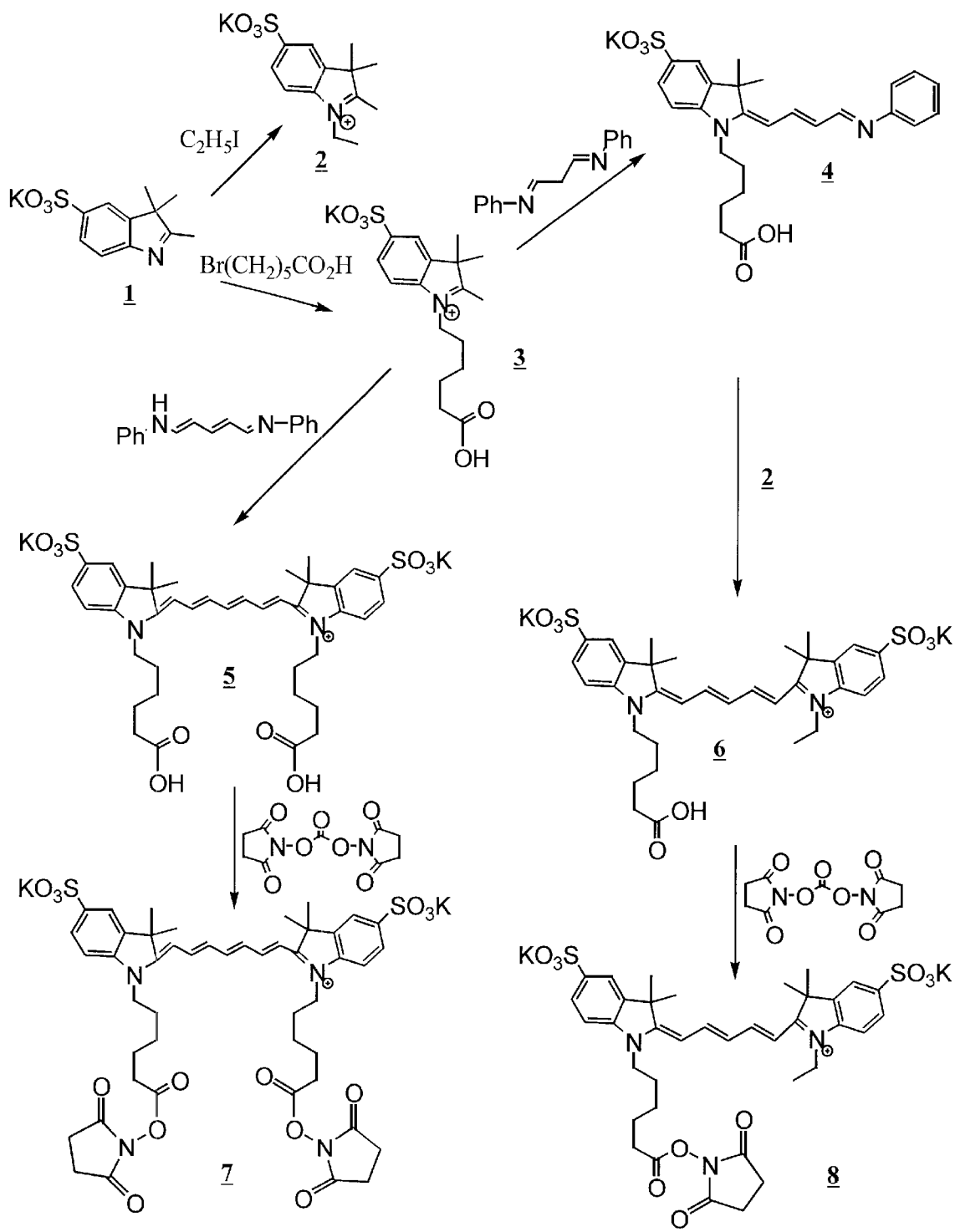
FIG. 1 depicts a reaction sequence used in the art to prepare cyanine dyes.

Various terms are used herein to refer to aspects of the present invention. To aid in the clarification of the description of the components of this invention, the following definitions are provided:

The term "analyte" refers to the compound or composition to be measured, the material of interest, which is usually a member of a specific binding pair and may be a ligand which is mono- or polyvalent. The analyte may be antigenic or haptenic, but may also take part in other specific binding interactions. It may be a single compound or a plurality of compounds which share at least one common epitopic or determinant site for specific binding interactions. Analytes include small molecule species such as drugs, low molecular weight organic species found in organisms, in the environment and the like. They also include larger materials such as polymeric materials, these materials may be monoepitopic, but often are polyepitopic, they include synthetic polymers, but will more commonly, in biological systems be poly (amino acids), including polypeptides and proteins; polysaccharides; nucleic acids, such as DNA, RNA or oligonucleotides; and combinations thereof. These materials may be found as components of bacteria, viruses, chromosomes, genes, mitochondria, nuclei, cell membranes and the like.

For the most part, the polymeric analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight. The nucleic acid materials typically have similar molecular weights.

The small molecule analytes, which are most commonly monoepitopic, will generally be from about 100 to 2,000 molecular weight, more usually from 125 to 1,000 molecular weight. The analytes of interest include, but are not limited to, drugs, metabolites, pesticides, pollutants and the like.

The term "member of a specific binding pair" ("sbp member") refers to one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormone-hormone receptors, nucleic acid duplexes, IgG-protein A, DNA-DNA, DNA-RNA, and the like, that are not typically classed as immunological pairs are included in the definition of specific binding pair. A conjugate is a specific binding pair. In certain situations an association or complex of molecular entities form an association requiring 3 or more molecular species. For the purposes of this invention, the reference to a specific binding pair also includes associations made up of more than two molecular species.

The term "ligand" as used herein refers to any organic compound for which a receptor naturally exists or can be prepared.

The term "receptor" (also referred to herein as "antiligand") refers to any compound or composition capable of recognizing a particular spatial and polar organization of a molecule, e.g., epitopic or determinant site. Illustrative receptors include, but are not limited to, naturally occurring receptors, e.g., thyroxine binding globulin, antibodies, enzymes, Fab fragments, lectins, nucleic acids, protein A, complement component Clq. and the like.

A "label" as used herein refers to a member of the signal-producing system that is conjugated to an sbp member. The label can be any bridged cyanine or squaraine dye as defined herein.

A "signal producing system" as used herein may have one or more components, at least one component being a dye or precursor of a dye. The signal-producing system includes all of the reagents required to produce a measurable signal including means for causing electronic excitation of the squaraine dye. A preferred means can be, for example, a He/Ne laser with an emission wavelength at 633 nm. However, other light sources having an excitation wavelength greater than 600 nm can also be employed. Other components of the signal-producing system can include enzymes, chemiluminescent compounds, quenchers, substrates, etc.

A "group" or "functionality" imparting water solubility or water-solubilizing groups refers to a functionality incorporated into a compound which imparts water solubility to the compound, that is, renders the compound soluble in water to an extent of at least one nanomolar. Such functional group or functionality, include but are not limited to, a sulfonate, phosphate, phosphonate, carboxylate, hydroxyl, amine, ether, amide and the like. The group imparting water solubility generally comprises from 1 to 30 atoms, preferably 1 to 12 atoms, other than hydrogen, which atoms are selected from the group consisting of carbon, oxygen, nitrogen, sulfur, phosphorus, and halogen of atomic number 9 to 53. Such group can be part of the dye prior to the formation of the conjugate of the dye and the sbp member. Consequently, the dye can be conjugated to a wide variety of sbp members including poly(amino) acids without significantly altering the water solubility of the sbp member or without having the spectroscopic properties of the dye adversely affected.

"Ancillary materials" refer to various other materials that will frequently be employed in an assay. For example, buffers will normally be present in the assay medium, as well as stabilizers for the assay medium and the assay components. Frequently, in addition to these additives, proteins may be included, such as albumins, or surfactant, particularly nonionic surfactant, binding enhancers, e.g., polyalkylene glycols, or the like.

The term "linking group" (also alternatively referred to herein as a "bridge") refers to the group that binds the dye to the spb member. The dye and the sbp member can be bound together either covalently or non-covalently. Covalent binding, however, is more common. Covalent binding can result from a bond or a linking group. A wide variety of linking groups may be employed to bond the dye and the sbp member. The choice of linking group will vary widely, depending upon the available functionalities or functionalities which may be present or readily introduced into the dye or sbp member, the desired length of the linking arm, the desirability of having the linking arm provide for a particular environment, chemical property or physical property, e.g., positively or negatively charged, solubility enhancement, dipole effects, or the like. The linking group preferably includes a non-oxo-carbonyl, carbamoyl, thiocarbamoyl, sulfonyl, amino, or a thio; particularly a functionality having a non-oxo-carbonyl and sulfur analogues thereof; as an active linking functionality for joining the sbp member to the fluorophore.

A "conjugated bridge" refers to a divalent organic functionality linking two regions of a molecule and having a plurality of unsaturations which electronically interact with one another, and/or with other unsaturation present in the other regions being linked.

As used herein "particles" are of at least about 50 nm and not more than about 50 microns, usually at least about 100 nm and less than about 25 microns, preferably from about 0.2 to 5 microns diameter. The particle may be organic or inorganic, swellable or non-swellable, porous or non-porous, preferably of a density approximating water, generally from about 0.7 to about 1.5 g/mL, and composed of material that can be transparent, partially transparent or opaque.

The organic particles will normally be formed of polymers, either addition or condensation polymers, which are readily dispersible in the assay medium. The organic polymers will also be absorptive or functionalizable so as to bind, either directly or indirectly, an sbp member.

The particles can be derived from naturally occurring materials, naturally occurring materials which are synthetically modified and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like. Inorganic polymers include silicones, glasses, available as Bioglas, and the like. Natural or synthetic assemblies such as liposomes, phospholipid vesicles, and cells can also be employed.

Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of being bound to a support or a compound of the invention through specific or non-specific covalent or non-covalent interactions. A wide variety of functional groups are available or can be incorporated. Functional groups include, but are not limited to, carboxylic acids, aldehydes, amino groups, cyano groups, ethylene groups, hydroxyl groups, mercapto groups and the like. The manner of linking a wide variety of compounds to particles is well known and is amply illustrated in the literature. (See, e.g., Cautrecasas (1970) J. Biol. Chem. 245:3059). The length of a linking group to a compound of the invention may vary widely, depending upon the nature of the compound being linked, the effect of the distance between the compound being linked and the particle on the binding of sbp members and the analyte and the like.

An organic group may be substituted. Most commonly this means that a hydrogen atom of the organic group has been replaced with a heteroatom-containing substituent such as a halo (Cl, Br, I, F) or an oxygen-containing group such as an ether, alcohol, aldehyde, ketone, acid or water, equivalent sulfur-containing groups and nitrogen-containing groups such as an amino or an amide. It can also mean that such a group has been inserted into the carbon chain or ring of an organic group.

The Dyes

The dyes of the present invention are novel fluorescent compounds. These dyes have an absorption maximum greater than 500 nm, preferably greater than 600 nm.

The compounds of this invention have the following general formula:

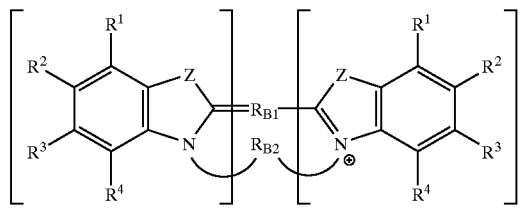

wherein $R_{B1}$ is a conjugated bridge of from about 3 to about 11 atoms in length;

$R_{B2}$ is a bridge of from about 6 to about 30 atoms in length; and

Z is selected from O, S, Se, N or —$CR^5R^6$; wherein $R^5$ and $R^6$ are each independently selected from a lower alkyl, which is defined to be an alkyl of from 1 to 4 carbons. Preferably both are methyl groups. $R^5$ and $R^6$ may be joined into a cycloalkyl of from 4 to about 8 carbons, as well. $R^5$ and $R^6$ may be substituted, if desired.

$R^1$, $R^2$, $R^3$, and $R^4$ are each independently selected from the group consisting of hydrogen, a lower alkyl, a substituted lower alkyl or a water-solubilizing group. Adjacent members of this group of Rs may be joined into an alkylene ring or may be formed into an aromatic group to provide two or three fused aromatic rings, with or without substitution.

In one embodiment $R_{B1}$ is a conjugated alkene chain of the formula —(CH)$n_1$— wherein $n_1$ is an integer of from 3 to 11. In this case, the dyes are referred to cyanine dyes and have the following structure:

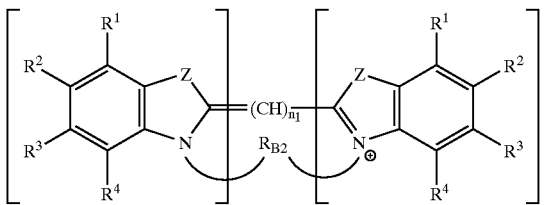

wherein $R^1$, $R^2$, $R^3$, $R^4$, $R_{B2}$, Z and $n_1$ are as previously defined. As is known in the art, the value selected for $n_1$ will have an effect on the emission wavelength for the dye. Thus, the emission wavelength can be tailored and adjusted by varying $n_1$.

In another embodiment $R_{B1}$ contains a cyclic structure, such as cyclohexane or the like, as depicted below:

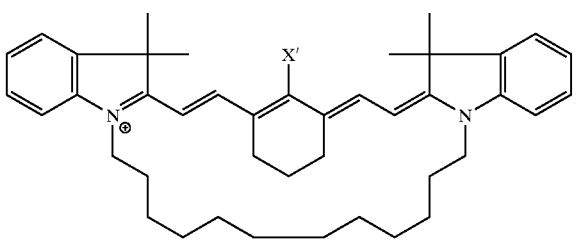

wherein X' is a halogen, alkyl, aryl and SR, wherein R is an alkyl or aryl substituent.

In another embodiment $R_{B1}$ contains a cyclic structure such as a squaraine or croconate structure or the like, as depicted below.

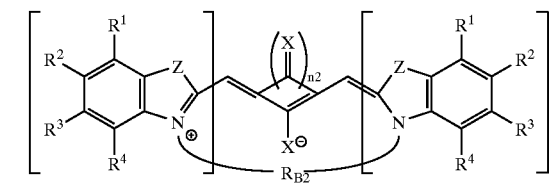

wherein $n_2$ is 1, 2 or 3; and

X is independently selected from the group consisting of O, S and Se;

The selection of $n_2$ and $R^5$ can have an effect on the wavelength of the fluorescent emission. When $n_2$ is 1 the dyes are referred to as squaraine dyes and have the following structure:

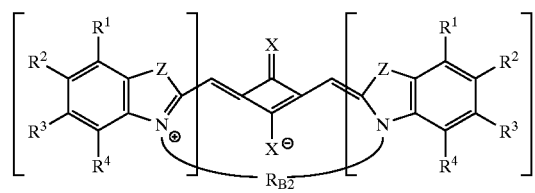

When $n_2$ is 2, the dyes are referred to as croconate dyes and have the following structure when X is oxygen:

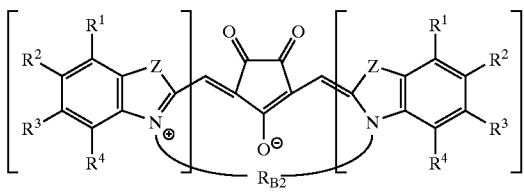

In each of the above structures, $R_{B2}$ is covalently attached between the two heterocyclic units. $R_{B2}$ can attach to the Z groups, to the N's in the heterocyclic structure or to $R^1$ through $R^4$ These three attachment patterns lead to the following structures respectively:

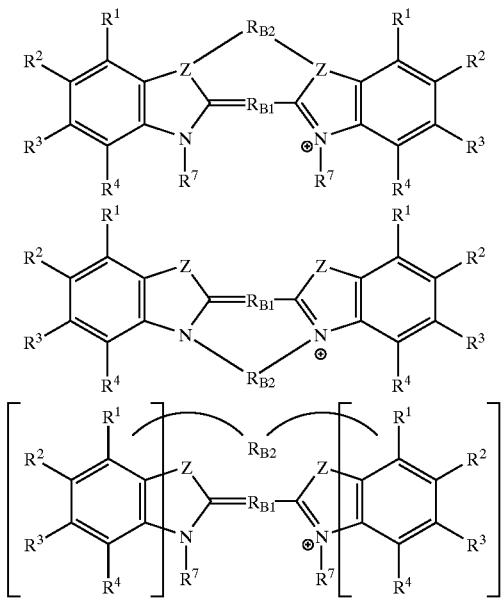

$R^7$ is an alkyl or a alkylene substituent (the two $R^7$'s could be also linked). $R_{B2}$ can be a simple alkylene linkage. It can also be a polyether or can include an amine or other nitrogen group in its chain. $R_{B2}$ can be substituted such as with water-solubilizing groups and/or with linking groups which provide an attachment point for coupling to the sbp member.

Note that the dyes of the present invention may be asymmetrical; i.e., the heterocycles attached by linking and bridging units need not be identical. For example, in any of the structures presented above, $R^1$ on the left hand side of the structure need not be identical to $R^1$ on the right hand side. Such asymmetrical dyes fall within the scope of the present invention.

A key function of $R_{B2}$ is to restrain the dye into a desired conformation to provide a desired emission wavelength and provide functionality for covalent linkage to proteins and nucleotides.

$R_{B2}$ has a chain length of from about 8 to about 30 atoms. More commonly $R_{B2}$ is from 10 to 28 and especially 12 to 28 atoms in length.

FIG. 2 depicts the structures of a number of representative dyes in accord with the invention.

Method of Preparation

The dyes of this invention are prepared as follows:

In a first step, the two heterocycles, or protected or precursor versions thereof, are covalently coupled to the $R_{B2}$ bridge. Thereafter the $R_{B1}$ conjugated bridge is covalently inserted between the two heterocycles.

The first step in which the heterocycles are coupled to the $R_{B2}$ linker is typically carried out under condensation conditions. In the case where the linker includes bromo leaving groups and the condensation proceeds through the elimination of HBr, it is commonly carried out at elevated temperatures from 100° C. to 200° C. in a high boiling solvent such as nitrobenzene or dichlorobenzene. It may be advantageous to have a detergent or other phase transfer catalyst present depending upon the solubility characteristics of the various reactants.

Figure 3:
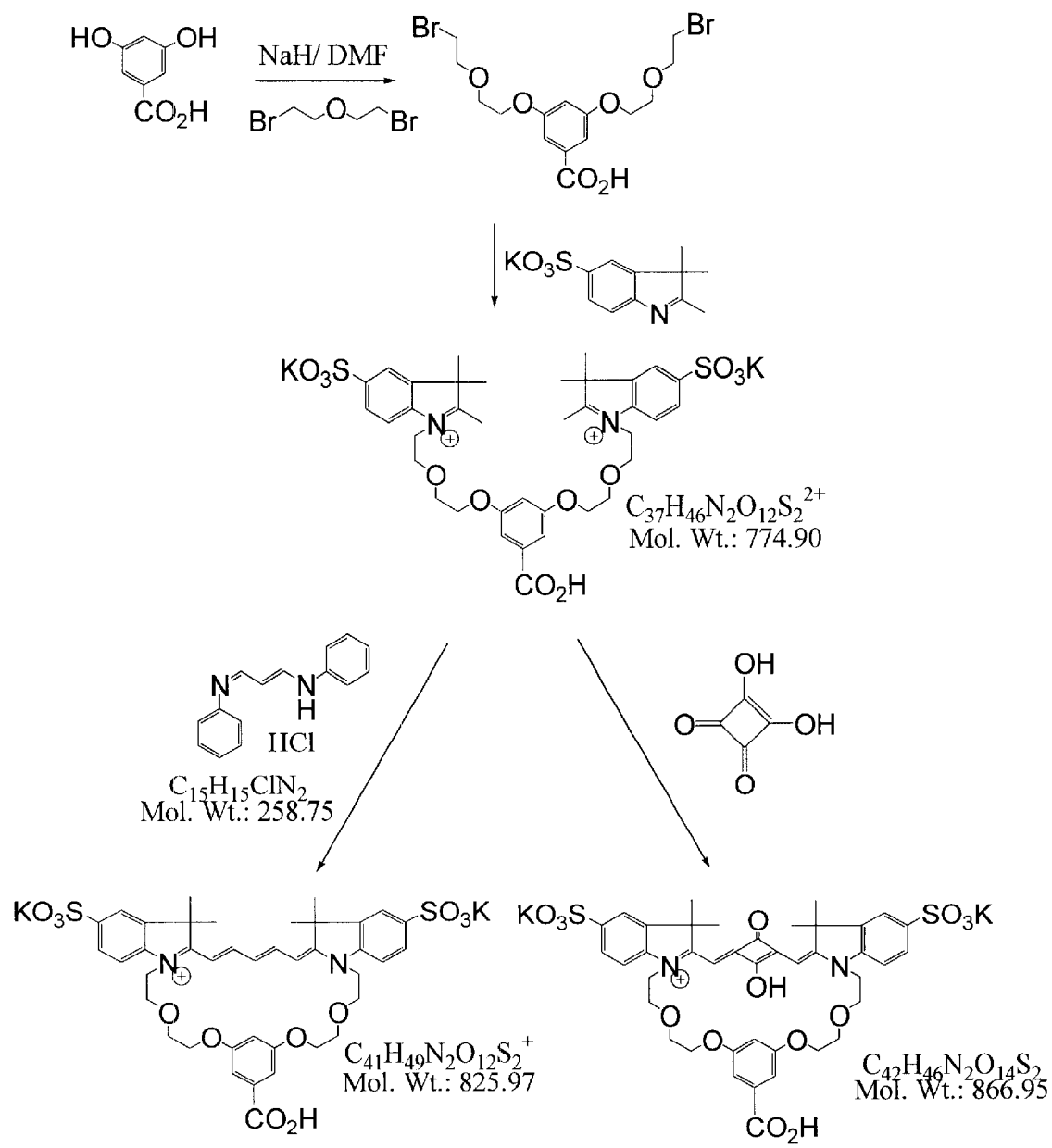
FIGS. 3, 4 and 5 illustrate three reaction sequences for making dyes bridged between their heterocyclic nitrogens.
Figure 4:
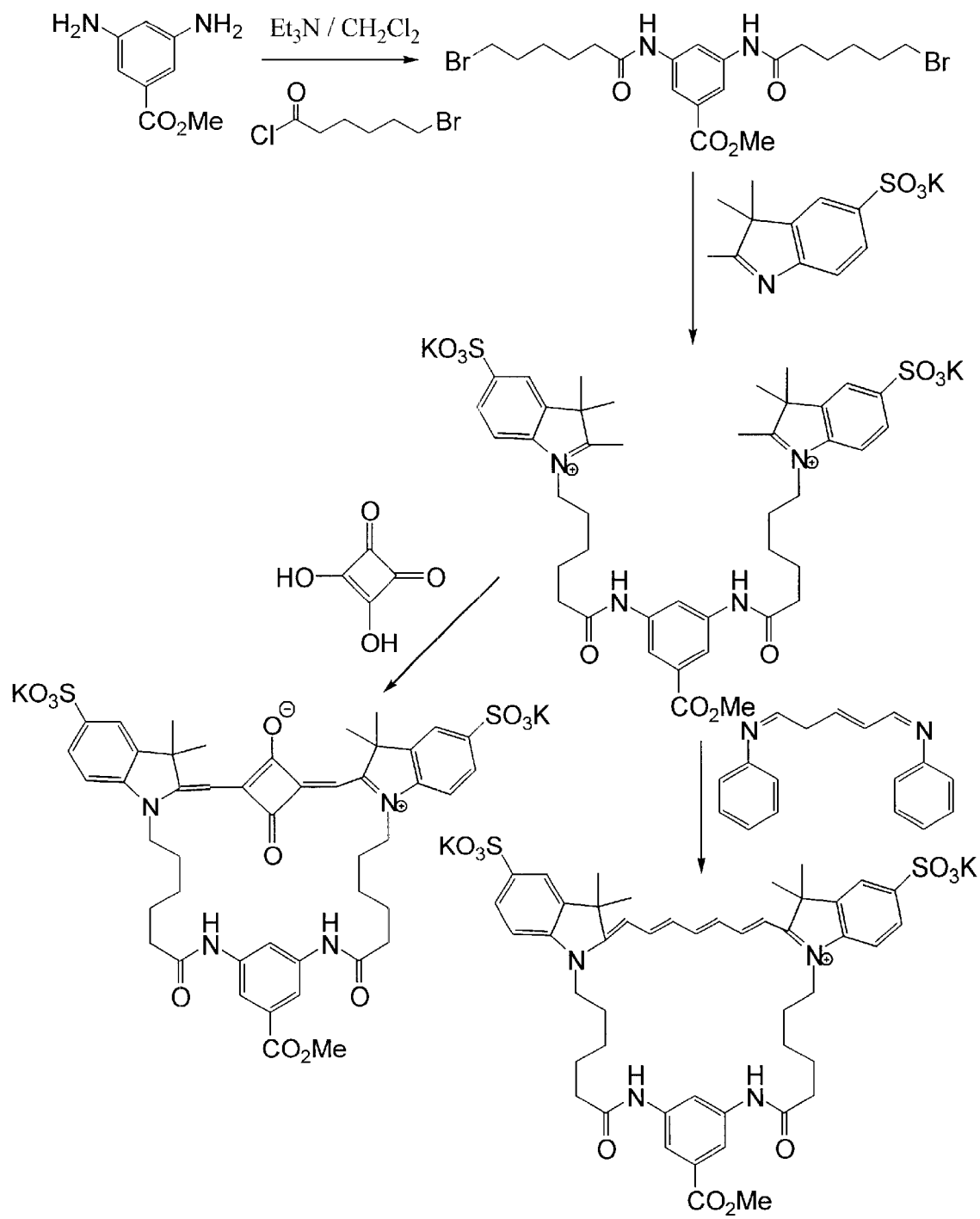
Figure 5:
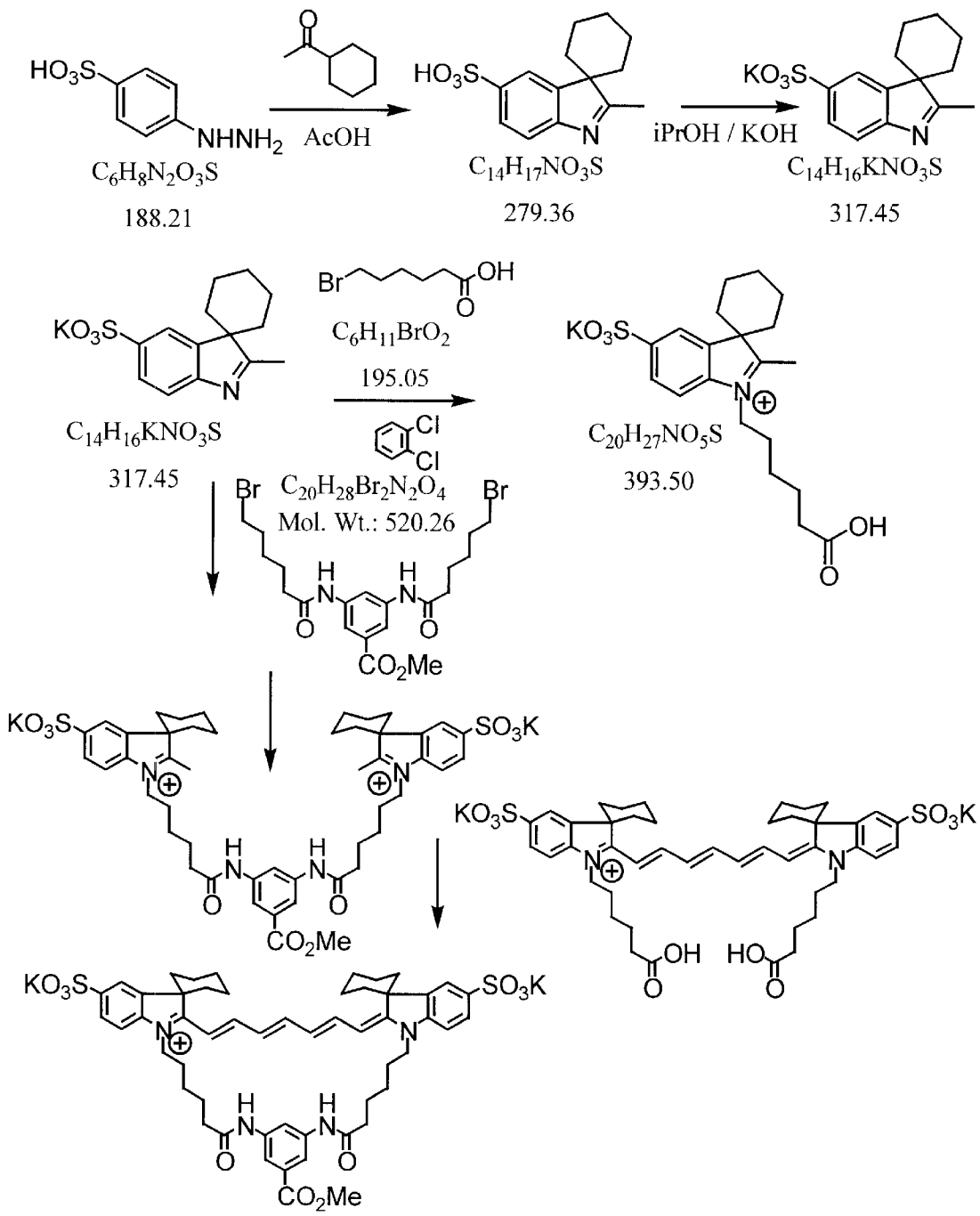
Figure 6:
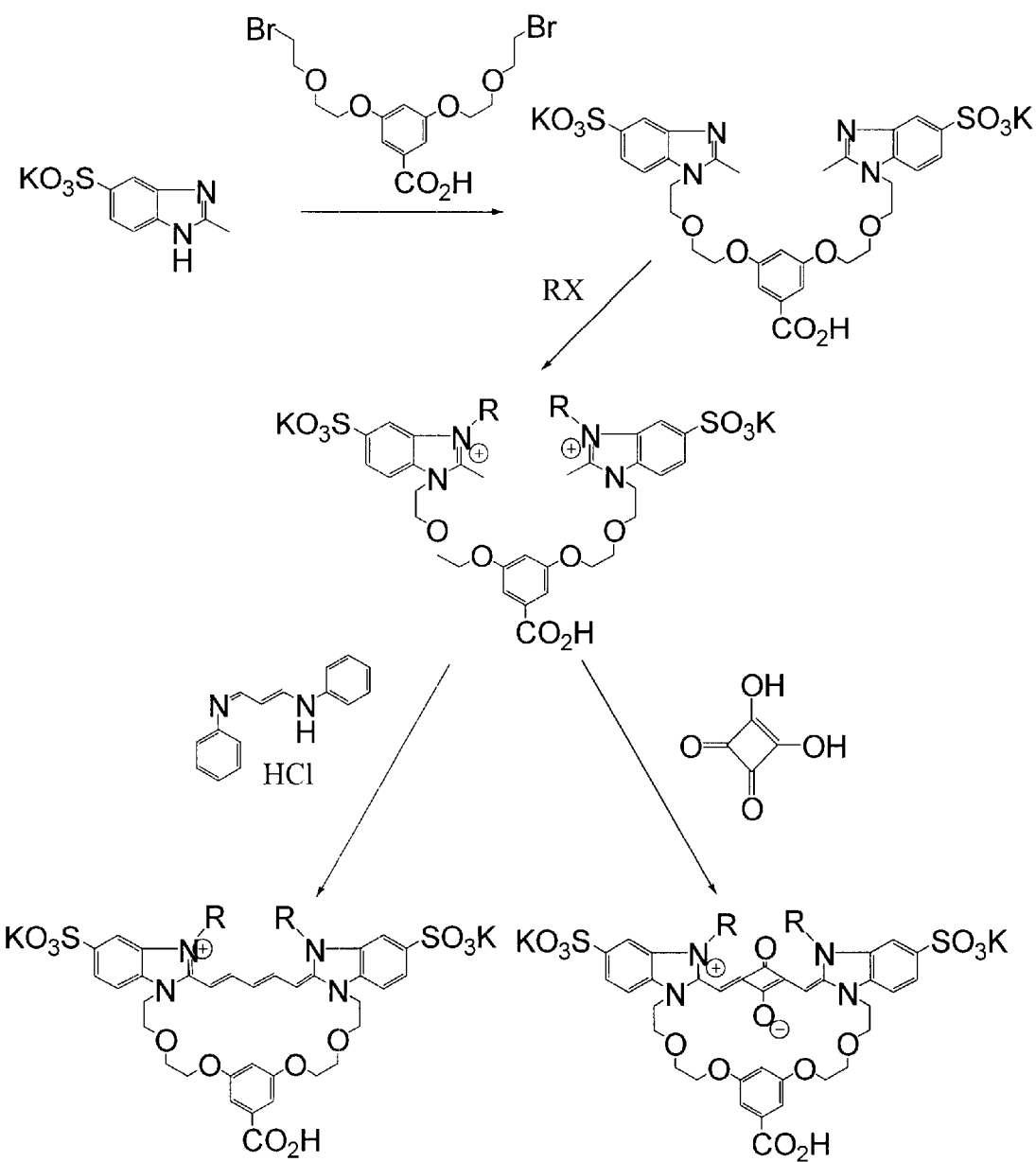
FIG. 6 illustrates a reaction sequence for making dyes bridged through their Z groups.
Figure 7:
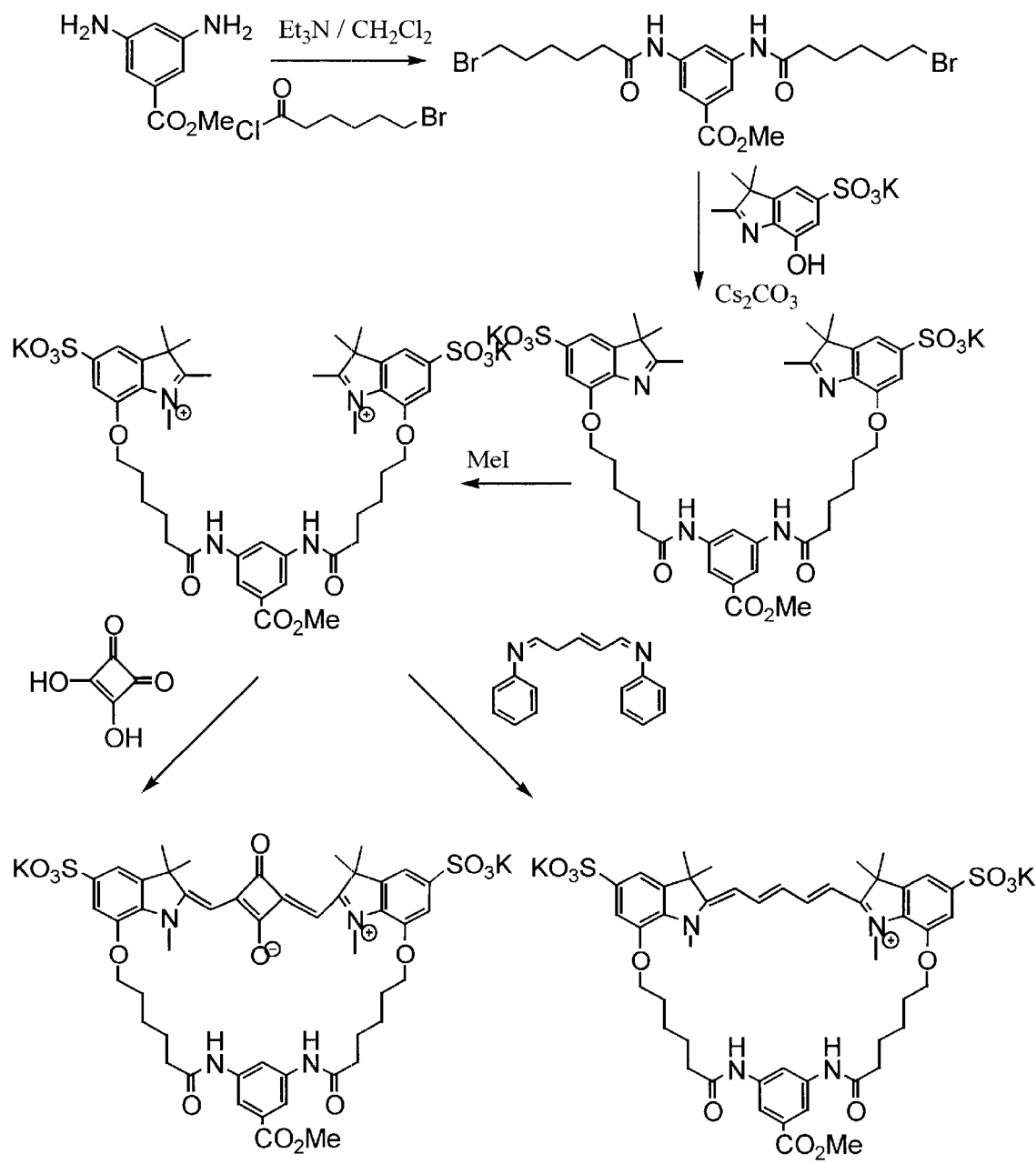
FIG. 7 illustrates a reaction sequence for making dyes bridged through their R groups.

In the second step, as depicted in FIGS. 3–5, the conjugated bridge $R_{B1}$ is added across the two heterocycles. In many cases this is done under dehydrating conditions designed to drive the removal of water. These conditions can also include a general acid-base catalysis system. These conditions can be attained using a Dean-Starke apparatus or an acetic-anhydride sodium acetate solvent system.

Six representative synthetic schemes are illustrated in FIGS. 3–8.

Please note, as would be recognized by one skilled in the art, that the illustrative synthetic methods presented herein could also be utilized to produce asymmetrical compounds (e.g., where $R^1$ on one heterocyclic moiety is different from $R^1$ on the other heterocyclic moiety). This could be done most simply by using different starting materials.

Dye-Ligand Conjugates

The dyes of the invention are conjugated with ligands which comprise the first element of one or more specific binding pairs, with the second element of the pairs being related to the analyte(s) of interest.

Most commonly, the second element of the specific binding pair and the analyte to which it is attached are present in an aqueous environment. In this case, if the dye itself is water soluble it is most common for the dye to include a linking group for covalently bonding to the first element of the specific binding pair. Usually, the dye includes a single binding group. These groups may be attached to the heterocyclic group through one of its R groups, X, its nitrogen or through $R_{B2}$.

In another embodiment, the fluorescent dye may be attached to or encapsulated within a particle. In this case, the particle may have water-solubilizing groups attached to it and may provide the necessary groups for binding to the first elements of the specific binding pairs. In this case, the dye plus particle is considered to be the dye-ligand conjugate.

Signal Producing Systems

The dyes of this invention and their dye-ligand conjugates can be employed as elements of signal producing systems. These systems include a sample zone in which a sample suspected of including one or more analytes are located. The dye-ligand conjugates are contacted with the sample in the zone to form one or more specific binding pairs between analytes and dye-ligand conjugates.

A source of electromagnetic radiation, typically a laser irradiates the sample and emission from the dye-ligand conjugate is detected. The art teaches a great number of specific binding pairs based on assay techniques employing prior fluorescent dyes. These assay techniques may be employed with the novel fluorescent dyes provided by the present invention.

The bridged dyes of the invention can be conjugated to sbp members by techniques that are known in the art. Such conjugation can be the result of direct bond formation between the squarate dye and the sbp member. On the other hand, a linking group as described above can be introduced into the squarate dye or the sbp member for attachment to the other component. A functionality for attachment such as carboxylic acid, hydroxyl, thio, amino, aldehydic, amido, activated ethylenes such as maleimide, sulfonic acids, and the like can be introduced into the dye or the sbp member if such functionality is not originally present in the dye or the sbp member. Methods of conjugation involving sbp members are described in e.g., U.S. Pat. No. 3,817,837, which is incorporated herein by reference in its entirety.

The compounds of the invention have properties that are very desirable for their use in assays. The compounds have high extinction coefficients, high quantum efficiencies, approaching one, chemical stability, and satisfactory Stokes shifts. Furthermore, where the compounds are to be used in the presence of serum or other composition, which is in itself fluorescent, the compounds absorb energy in a substantially different range from that absorbed by the other compounds in the medium. As mentioned above, the present compounds have an absorption maximum greater than 600 nm.

One aspect of the present invention involves an assay for a material of interest in a sample suspected of containing the material of interest. In the assay a fluorescent compound is employed to generate a signal in relation to the presence or amount of the material of interest in said sample and an energy source for excitation of said fluorescent compound is also employed. The improvement in such assay comprises employing a bridged dye of the invention, particularly a water compatible dye having an absorption maximum greater than 600 nm, as the fluorescent compound and a helium/neon laser as the energy source. The present dyes can be rendered water compatible by incorporating a group or functionality imparting water solubility into the squarate dye. Alternatively, the squarate dye can be rendered water compatible by employing about 0.01 to 10%, of a detergent such as Triton X-100 or sodium dodecyl sulfate, $1\times10^{-4}$ to $1\times10^{-2}$ M cyclodextrin or the like, in the assay medium. In another alternative, 0.02 to 20 $\mu$m latex particles or particles such as liposomes, cells and the like can be stained with the bridged dye to provide water compatibility.

Another aspect of the present invention involves an improvement in an assay for an analyte in a sample suspected of containing said analyte where the analyte is an sbp member. The method involves an sbp member conjugated to a dye and the improvement of the invention comprises employing as the dye a bridged dye.

For example, a fluorescent assay can employ as a reagent a fluorescent compound conjugated to a member of a specific binding pair. Such assay is for the determination of an analyte which is also a member of a specific binding pair. The binding of the conjugate to the analyte or a specific binding pair member complex of the analyte is indicative of the presence of the analyte. The present improvement comprises employing in the fluorescent assay a reagent that is a bridged dye conjugated to a member of a specific binding pair. Another example is a method for detecting the presence of a determinant site or a receptor by employing a fluorescent reagent having a fluorescent compound bound to a member of a specific binding pair. The binding of the fluorescent reagent to the determinant site or the receptor, or a specific binding pair member complex of the determinant site or the receptor, is determined as indicative of the presence of the determinant site or the receptor. The improvement of this invention comprises employing a fluorescent reagent that is a conjugate of a squarate dye and a member of a specific binding pair. The method has particular application where the determinant site or receptor is associated with a cell such as, e.g., being present on the cell surface.

The present conjugates can be used for determining qualitatively, semiquantitively or quantatively an analyte in a sample. Where compounds are to be detected in physiological fluids, the sample may include serum, urine, saliva, lymph or the like. Where the compound of interest is involved in chemical processing or ecological concerns, the sample may be an aqueous medium, or may be obtained by extraction from an organic medium, soil, inorganic mixtures, or the like.

Another reagent in the assay can be a compound of the invention where the sbp member is a receptor for the analyte.

As indicated previously, the compounds of this invention can include its bridged dyes conjugated to compounds which may be measured by known immunoassay techniques. The conjugates are reagents which compete in an assay medium for the analyte in a sample. Therefore, the conjugate retains a sufficient proportion of the structure of the analyte to be able to compete with the analyte for a receptor for analyte.

The assays may involve a change of spectroscopic properties due to a change in environment about the spectroscopically active compound or the bringing together of a fluorescer-quencher pair within sufficient proximity for the quencher to interact with the fluorescer. Alternatively, methods can be employed which involve the separation of associated and unassociated fluorescer and the detection of the fluorescer in one or both of the fractions.

In carrying out the method an aqueous medium will normally be employed. Other polar solvents may also be employed, usually oxygenated organic solvents of from 1 to 6, more usually from 1 to 4 carbon atoms, including, but not limited to, alcohols, ethers and the like. Usually these cosolvents will be present in less than about 40 weight percent, more usually in less than about 20 weight percent.

The pH for the medium will usually be in the range of about 4 to 11, more usually in the range of about 5 to 10, and preferably in the range of about 5.4 to 9.5. The pH is chosen so as to maintain a significant level of binding between sbp members while optimizing signal producing proficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the method and usually constant temperatures during the period of the method. The temperatures for the determination will generally range from about 10° C. to 50° C., more usually from about 15° C. to 40° C.

The concentration of analyte which may be assayed will generally vary from about $10^{-4}$ to $10^{-15}$ M, more usually from about $10^{-6}$ to $10_{-13}$ M. Considerations such as whether the assay is qualitative, semi-quantitative or quantitative, the particular detection technique, and the concentration of the analyte will normally determine the concentration of the other reagents.

While the concentrations of the various reagents will generally be determined by the concentration range of interest of the analyte, the final concentration of each of the reagents will normally be determined empirically to optimize the sensitivity of the assay over the range of interest. The total binding sites of the members of the specific binding pair which are complementary to the analyte will be not less than about 0.1 times the minimum concentration of interest based on binding sites of the analyte and not more than about 10,000 times the maximum concentration of interest based on analyte binding sites, usually about 0.1 to 1000 times, more usually about 0.3 to 10 times the maximum concentration of interest. For ligand analyte, where labeled ligand is employed, the concentration of interest and not greater than 100, usually not greater than 10, times the maximum concentration of interest.

The concentration of the compound of the invention in the assay medium is dependent on the type of assay, heterogeneous or homogeneous, competitive or direct, etc. Normally the compound of the invention will be present in the assay medium in a concentration about $10^{-6}$ to $10^{-15}$, usually about $10^{-8}$ to $10^{-13}$ M.

The order of addition of the various reagents may also vary and is dependent on many of the same considerations mentioned above.

The present assay method has application both to heterogeneous and homogeneous assays. Exemplary heterogeneous assays are found in U.S. Pat. Nos. 4,256,834 and 4,261,968. Homogeneous immunoassays are exemplified by immunofluorescence methods such as those disclosed in U.S. Pat. No. 3,993,345, enzyme channeling techniques such as those disclosed in U.S. Pat. No. 4,233,402, and other enzyme immunoassays as discussed in U.S. Pat. No. 3,817,837. The assay can be competitive or direct and can involve compounds of the invention that are either labeled ligand or labeled receptor.

In one approach in accordance with the invention for detecting the presence or amount of analyte in a sample suspected of containing said analyte wherein said analyte is an sbp member consisting of ligand and its complementary receptor the method comprises: (1) combining in an assay medium the sample, as described above, a conjugate of the dye and an sbp member, and a second sbp member, wherein the two sbp members are complementary to the analyte; and (2) determining the effect of said sample on the fluorescence of the spb/dye conjugate as related to the presence or amount of analyte in said sample.

The second sbp member can be conjugated to a compound capable of quenching the fluorescence of the conjugate when both sbp members are bound to the analyte. Alternatively, the second sbp member can be bound to a particle or to a surface or support to permit separation of conjugate that binds to the support from the conjugate remaining in solution.

For example, in one technique, a quencher for the dye is employed. One reagent is a compound of the invention comprising a conjugate of a squarate dye and an analog of a ligand analyte. Another reagent is a conjugate of quencher and an sbp member that is a receptor for the analyte. The ligand analyte in the sample and the ligand analyte analog in the reagent compete with receptor for analyte. When the receptor for analyte binds to the labeled ligand analyte analog, the fluorescer and quencher are brought within quenching distance. A similar assay employing fluorescent compounds not within the scope of this invention is extensively described in U.S. Pat. No. 3,996,345. The assay technique is described beginning with column 17 and ending at column 23, which description is incorporated herein by reference. The ratios of fluorescent compound to ligand and receptor is described in the above-cited patent at columns 4–6, which description is incorporated herein by reference.

In a related but different approach one reagent can be a compound of the invention that is a conjugate of a squarate dye and a receptor for the ligand analyte. Another reagent is a conjugate of a quencher for the dye and a receptor for the ligand analyte. When the two reagents above are combined with the sample and brought together by the presence of ligand analyte, the squarate dye and the quencher are brought within quenching distance. A typical quencher can be, e.g., gallocyanine, which can be conjugated through an amide bond to an sbp member.

The assay is carried out by combining the bridged dye conjugate and the quencher conjugate in conjunction with the sample. The fluorescence is determined in comparison to an assay medium having a known amount of analyte.

In another example the compound of the invention is a conjugate of a bridged dye and a receptor for the ligand analyte. Ligand or ligand analog is bound to a support or to a particle. Similar assays are described in U.S. Pat. No. 4,275,149. These assays are predicated upon having the fluorescer molecule available in bulk solution for interaction with a signal modulator or bound to a particle, where the particle enviromnent prevents the interaction. Alternatively, the particle can provide an environment which modulates the fluorescent signals when the fluorescer conjugate is bound to the particle.

Another approach involves steric exclusion in that receptors for the ligand and for the squarate dye are employed, where simultaneous binding of the receptor for the ligand and receptor for the dye is inhibited. Furthermore, when the receptor for the dye is bound to the dye, the fluorescence of the dye is substantially diminished. Further reduction, if not complete inhibition of fluorescence, can be achieved by conjugation of quencher to receptor for the dye. A similar assay is extensively described in U.S. Pat. No. 3,998,943, issued Dec. 21, 1976. The assay is described in columns 3–5 of the subject patent, which description is incorporated herein by reference.

Generally, the method involves combining in an assay medium the sample suspected of containing the analyte, the conjugate of the sbp member and the dye, and other reagents in accordance with the particular assay protocol chosen. The sample is then exposed to a source of excitation. The fluorescence is determined either as a rate or equilibrium mode, readings being taken within about 1 second to 1 hour after all materials have been combined for a rate mode, while for an equilibrium mode, readings may be taken for as long as up to about 24 hours or longer.

As a matter of convenience, the reagents employed in the present invention can be provided in a kit in packaged combination with predetermined amounts of reagents for use in saying for an analyte in a sample. The reagents will include a compound of the invention as disclosed above, and, where appropriate, conjugates of quenchers and sbp members or other reaction partners for the compound of the invention required to provide the detectable signal. In addition, other additives such as ancillary reagents may be included. The relative amounts of the various reagents may be varied widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay.

This invention will be further described by the following examples. These are intended to illustrated the invention and are not to be construed as limiting its scope.

EXAMPLES

Materials and Methods

4-Hydrazino benzenesulfonic acid; glutaconic aldehyde dianilide hydrochloride; 6-bromohexanoyl chloride; 3-methyl-2-butanone; 1,2-dichlorobenzene and methyl 3,5-diaminobenzoate were purchased from Lancaster. Malonaldehyde bis(phenylimine) dihydrochloride; 3,5-dihydroxy benzoic acid; 2-bromoethyl ether; sodium hydride; 3,4- dihydroxy-3-cyclobutene-1,2-dione (squaric acid); 2,3,3-trimethyl indolenine; disuccinimidyl carbonate and 1,12-dibromododecane were purchased from Aldrich. 2,3,3-Trimethyl benzindolenine was purchased from Acros.

Silica gel used for chromatography was Whatman 230-400 ASTM, purchased from VWR Scientific Products while analytical (250 microns) and preparative (1000 microns) Analtech plates were purchased from Aldrich and VWR Scientific products. Octadecyl reverse phase (C18 RP) silica plates were from Aldrich, while the C18RP silica gel was purchased from Pharmacia.

$^1$H NMR was recorded on a GE Nt300 MHz or 360 MHz NMR Spectrometer (Acorn NMR, Fremont Calif.). All chemical shifts are reported in ε units downfield of tetramethyl silane(TMS). Splitting patterns are designated as follows; s, singlet; d, doublet; t, triplet; q, quartet; m, multiplet and b, broad.

Fast atom bombardment mass spectrometry (FAB/LSIMS) was performed on a Micromass 70S or ZAB-SEQ at the University of California, Berkeley. Nitrobenzyl alcohol (NBA) or thioglycerol (TG) and glycerol (G) were typically used as the matrix.

UV-Visible absorption spectra were recorded on Shimadzu UV-2401PC Spectrophotometer, while fluorescence measurements were performed Spex-Fluorlog2 Fluorometer (Instrument S.A. Inc.).

Example 1

Preparation of Dibromo Diethoxy Benzoic Acid (9)

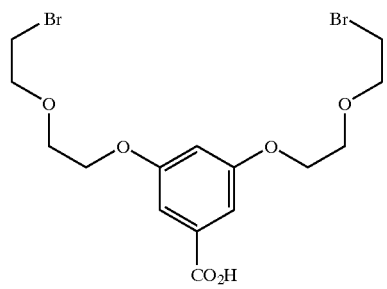

A solution of 3,5-dihydroxybenzoic acid (308 mg, 2.0 mmol) in anhydrous DMF (10 mL) was stirred under argon. Sodium hydride (60%, 250 mg, 6.2 mmol) was gradually added in batches allowing the effervescence to subside after each addition. After 10 minutes bis(bromoethyl) ether (7.0 g, 30 mmol) was added and the mixture was stirred under argon at room temperature for 4 hours and then refluxed for 70 hours. The crude reaction mixture was acidified with dilute HCl to a pH of 2.0 and extracted with $CH_2Cl_2$ (3×20 mL). The organic phases were combined and dried over anhydrous $Na_2SO_4$. Concentration followed by chromatography on silica with a MeOH gradient (0–10%) in $CH_2Cl_2$ gave 320 mg of the dialkylated product (9). $R_f$ 0.3, (silica 5% MeOH/$CH_2Cl_2$). $^1$H NMR (CDCl$_3$, 300 MHz); δ 7.14 (d, 2H, J=1.2Hz), 6.58 (t, 1H, J=1.2Hz), 4.44 (t, 4H, J=7.2Hz), 3.85 (m, 8H), 3.54 (t, 4H, J=6.8Hz).

Example 2:

Preparation of Dibromide (10)

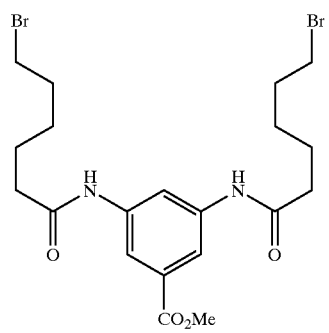

A solution of 3,5-diaminomethylbenzoate (4.2 g, 25 mmol) in $CH_2Cl_2$ (20 mL) was treated with (5.2 g, 51 mmol) of Et$_3$N under argon. The solution was stirred and cooled to 0° C. A solution of 6-bromohexanoyl chloride (10.7 g, 50 mmol) in $CH_2Cl_2$ (10 mL) was then added dropwise from an addition funnel. The rate of addition was such that the temperature of the reaction mixture did not rise above 5° C. After all the acid chloride had been added the reaction mixture was stirred for 16 hours and allowed to attain ambient temperature. The reaction mixture was washed with a cold solution of NaHCO$_3$ (0.1 M, 10 mL) and the organic phase was separated and concentrated to yield a yellow oil. Chromatography on silica with MeOH in $CH_2Cl_2$ afforded 8.7 g (67%) of the dibromide 10 as a fluffy light yellow solid. $^1$H NMR (CDCl$_3$, 360 MHz) δ 8.33 (bs, 2H), 8.05 (t, 1H, J=1.2Hz), 7.86 (d, 2H, 1.2Hz), 3.85 (s, 3H), 3.37 (t, 4H, J=6.8Hz), 2.36 (t, 4H, J=7.2Hz), 1.86 (m, 4H), 1.68 (m, 4H), 1.46 (m, 4H). MS (FAB, NBA) calculated for $C_{20}H_{28}Br_2N_2O_4$, 520; found 521(M+H$^+$, 100%).

Example 3

Preparation of 2,3,3-trimethylindolenine-5-sulfonic Acid (11)

2,3,3-Trimethylindolenine-5-sulfonic acid (11) was prepared by the method of Majumdar et al. Bioconjugate Chemistry 105:1993. $^1$H NMR (D$_2$O/CD$_3$OD, 300 MHz) δ 7.83 (d, 1H, J=1.8Hz), 7.80 (dd, 1H, J=8.4Hz, 1.8Hz), 7.45 (d, 1H, J=8.4Hz), 2.3 (s, ~2.5H), 1.35(s, 6H).

The potassium salt (1) (see FIG. 1) was prepared by treating a solution of the sulfonic acid in MeOH with a saturated solution of KOH in isopropanol. The yellow precipitate was dried under vacuum at 60° C. Rf 0.5 (C18RP silica, H$_2$O). $^1$H NMR (D$_2$O, 300 MHz) δ 7.15 (d, 1H, J=1.2Hz), 7.10 (dd, 1H, J=7.0Hz, 1.2Hz), 6.52 (d, 1H, J=7.0Hz), 2.25 (s, 3H), 1.36(s, 6H).

Example 4

Preparation of Diamino Methyl Benzoate Bridged bis(2,3, trimethyl indoleninium sulfonate) (12)

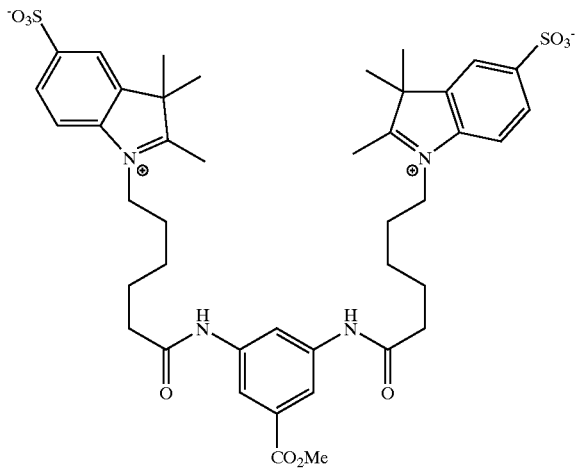

12

The potassium salt of trimethylindolenium sulfonate (1) (560 mg, 2.0 mmol) in 1,2-dichlorobenzene (5 mL) was treated with dibromide 10 (520 mg, 1.0 mmol) and the mixture heated at 140° C. for 24 hours while being stirred under argon. The pinkish purple reaction mixture was then allowed to cool. The solvent was carefully decanted and the crude product triturated with hot ethyl acetate until free powder was obtained. The solid was filtered and washed with $CH_2Cl_2$ to yield 820 mg (90%) of a hygroscopic pink colored material, compound 12. $R_f$(0.8, 20% MeOH in $H_2O$, C18 RP silica). $^1$H NMR (DMSO-$d_6$, 300 MHz) δ 8.23 (bs, 2H), 7.70–8.00 (m, 3H), 7.86 (s, 2H), 4.52 (bt, 4H,), 3.80 (s, 3H), 3.80 (s, 3H), 2.8 (s, exchanged with D), 2.32 (t, 4H, J=7.2Hz), 1.88 (m, 4H), 1.72 (s, 6H), 1.40–1.66 (m, 8H). MS(FAB, DMSO+NBA) calculated for $C_{42}H_{52}N_4O_{10}S_2$, 836; found 837 (M+H$_+$, 30%).

Example 5

Preparation of Dioxo Benzoic Acid Bridged bis(2,3, trimethyl indoleninium sulfonate) (13)

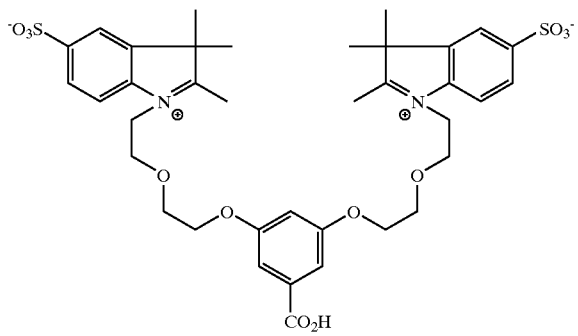

13

The potassium salt of trimethylindolenium sulfonate (1) (112 mg, 0.4 mmol) in 1,2-dichlorobenzene (1 mL) was treated with dibromide 9 (92 mg, 0.2 mmol) and the mixture was heated at 140° C. for 24 hours in a sealed tube. The reaction mixture was allowed to cool and transferred to a flask by washing the sealed tube with ethyl acetate. The reaction mixture was then refluxed for 2 hours, cooled and triturated with ethyl acetate until free powder was obtained. The solid was isolated by centrifugation followed by filtration and washed with $CH_2Cl_2$ to yield 144 mg (90%) of the diquarternary salt 13 as a hygroscopic pink colored material. $R_f$(0.4, 20% MeOH in $H_2O$, C18 RP silica). δ$_{max}$ ($H_2O$) 272 nm. $^1$H NMR ($D_2O$, 300 MHz) δ 8.07 (s, 2H), 8.00 (dd, 2H, J=7.2Hz, 1.2Hz), 7.04–7.24 (m, 5H), 4.62 (bs, 4H), 4.20 (m, 12H), 1.58(s, 12H). Protons at C-2 (Me) of indoleninium were exchanged. MS(FAB, TG/G) calculated for $C_{37}H_{44}N_2O_{12}S_2$, 772; found 795 (M+Na$^+$, 10%).

Example 6

Preparation of Hydrophilic Bridged Squarylium Dye (14)

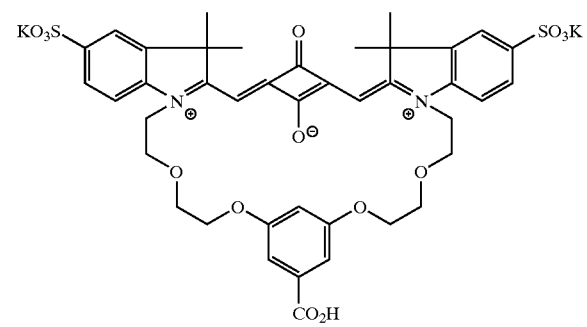

14

A mixture of squaric acid (11.4 mg, 0.1 mmol) and the bridged diquaternary salt 13 (80 mg, 0.1 mmol) in n-butanol (2 mL) and toluene (1 mL) were heated at reflux for 8 hours. The reaction was monitored spectrophotometrically by the appearance of a peak at 632 nm (water). The crude reaction mixture was concentrated and purified by preparative TLC (C18RP silica, 20% MeOH in $H_2O$) to yield 56 mg of a blue colored solid. δ$_{max}$ (PBS buffer) 632 nm (e=250,000); δ$_{ex}$ 633 nm; δ$_{em}$ 646 nm.

This procedure gave the butyl ester of the squarylium dye. Hydrolysis with $K_2CO_3$ in MeOH/$H_2O$ (5 mL, 0.1 M) gave the acid which was purified first by preparative TLC (C18 RP silica, MeOH/$H_2O$) and then by ion exchange chromatography (Dowex 50WX8–200, strongly acidic cation) to give the benzoic acid bridged squarylium dye 14. δ$_{max}$ (PBS) 632 nm; δ$_{em}$ 646 nm. MS (FAB, TG/G) calculated for $C_{42}H_{44}K_2N_2O_{14}S_2$, 942; found 965 (M+Na$^+$, 35%).

Example 7

Preparation of Bridged Squarylium Dye (15)

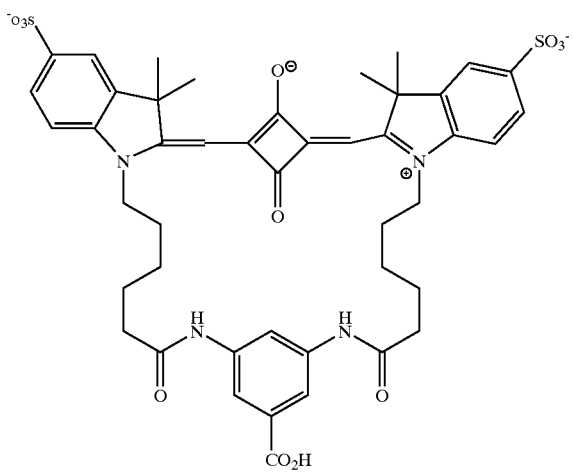

A mixture of squaric acid (114 mg, 1.0 mmol) and the bridged diquartemary salt 12 (840 mg 1.0 mmol) in n-butanol (2 mL) and toluene (1 mL) were heated at reflux for 4 hours. The reaction was monitored spectrophotometrically by the appearance of a peak at 632 nm (water). The crude reaction mixture was concentrated and purified by preparative TLC (C18RP silica, 20% MeOH in $H_2O$) to yield 610 mg of a blue colored solid. $\delta_{max}$ (PBS buffer) 632 nm (e=250,000); $\delta_{ex}$ 633 nm; $\delta_{em}$ 646 nm.

Hydrolysis with $K_2CO_3$ in MeOH/$H_2O$ (20 mL, 0.1 M) for 48 hours gave the acid which was purified first by preparative TLC and then by ion exchange chromatography (Dowex 50WX8–200, strongly acidic cation) to give the benzoic acid bridged squarylium dye 15. $\delta_{max}$ (PBS) 632 nm; $\delta_{em}$ 646 nm. $^1$H NMR ($D_2O$, 300 MHz) $\delta$ 7.86–7.92 (m, 5H), 7.32–7.54 (m, 2×2H), 6.02 (bs, ~2H), 4.05 (bt, 4H), 2.23 (t, 4H J=7.2Hz), 1.26–1.92 (m, 24H). MS(FAB, TG/G) calculated for $C_{45}H_{46}N_4O_{12}S_2^{-2}$, 898; found 944 (M+2Na$^+$, 20%).

Example 8

Preparation of Bridged Pentamethine Indoleninium Cyanine Dye (16)

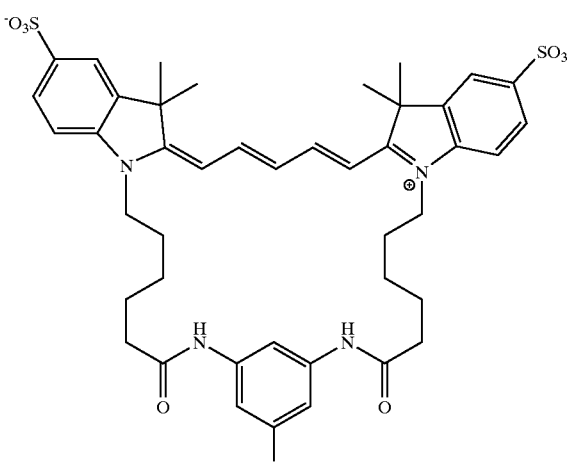

A mixture of malonaldehyde phenylimine hydrochloride salt (260 mg, 1.0 mmol) and the bridged diquartemary salt 12 (840 mg 1.0 mmol) in acetic anhydride (5 mL) and sodium acetate trihydrate (100 mg) were heated at reflux for 4 hours. The reaction was monitored spectrophotometrically by the appearance of a peak at 648 nm (water). The crude reaction mixture was concentrated and purified by preparative TLC (C18RP silica, 20% MeOH in $H_2O$) to yield 720 mg of a blue colored solid. $\delta_{max}$ (PBS buffer) 648 nm (e=250,000); $\delta_{ex}$ 648 nm; $\delta_{em}$ 674 nm.

Hydrolysis with $K_2CO_3$ in MeOH/$H_2O$ (20 mL, 0.1 M) for 48 hours gave the acid which was purified first by preparative TLC and then ion exchange chromatography (Dowex 50WX8–200, strongly acidic cation ) to give the benzoic acid bridged pentamethine indoleninium cyanine dye 16.

Example 9

Preparation of Bridged Heptamethine Indoleninium Cyanine Dye (17)

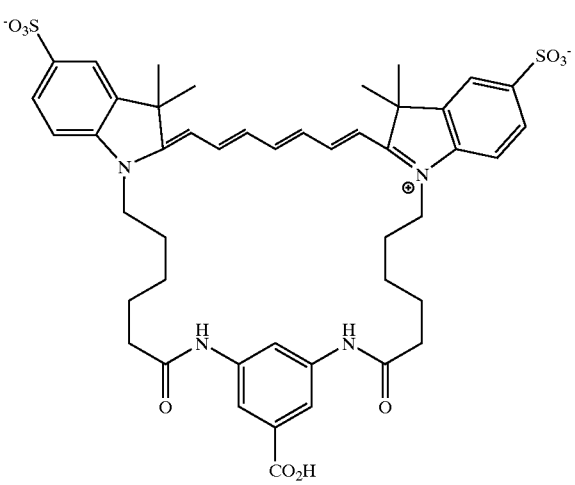

A mixture of glutaconic aldehyde dianilide hydrochloride (285 mg, 1.0 mmol) and the bridged diquartemary salt 12 (840 mg 1.0 mmol) in acetic anhydride (5 mL) and sodium acetate trihydrate (100 mg) were heated at reflux for 4 hours. The reaction was monitored spectrophotometrically by the appearance of a peak at 748 nm (water). The crude reaction mixture was concentrated and purified by preparative TLC (C18RP silica, 20% MeOH in $H_2O$) to yield 520 mg of a greenish blue colored solid. $\delta_{max}$ (PBS buffer) 748 nm; $\delta_{ex}$ (PBS) 748 nm; $\delta_{em}$ (PBS) 780 nm.

Hydrolysis with $K_2CO_3$ in MeOH/$H_2O$ (20 mL, 0.1 M) for 48 hours gave the acid which was purified first by preparative TLC (C18RP silica, 20% MeOH in $H_2O$) and then ion exchange chromatography (Dowex, 50WX8–200, strongly acidic cation) to give the benzoic acid bridged heptanethine indoleninium cyanine dye 17.

Example 10

Synthesis of C12 Linked 2,3,3-trimethyl-indolenine (18)

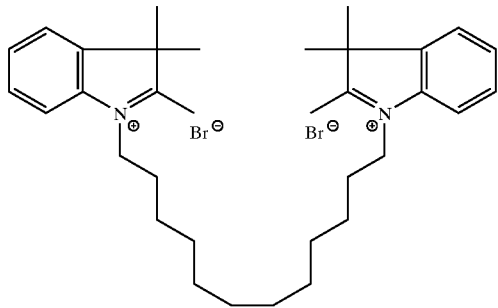

Dibromododecane (4.3 g, 13.3 mmol) was added to neat 2,3,3-trimethyl indolenine (8.5 g, 54.3 mmol). The solution was heated to reflux and stirred for 24 hours. The solution was then cooled to room temperature and the crude reaction mixture was loaded onto a silica gel column and chromatographed (0 to 20% MeOH/CH$_2$Cl$_2$). The desired fractions of product 18 were collected and concentrated to yield a hygroscopic purple glassy solid. Yield 7.0 g (79%). Rf- 0.5 (5% MeOH/CH$_2$Cl$_2$). $^1$H NMR (CDCl$_3$, 360 MHz) δ 7.57 (m, 8H), 4.75 (t, 4H, J=7.4Hz), 3.12 (s, 6H), 1.95 (m, 4H), 1.51 (s, 12H), 1.26–1.45 (m, 16H).

Example 11

Synthesis of Decanyl Bridged Indoleninium Pentamethine Dye (19)

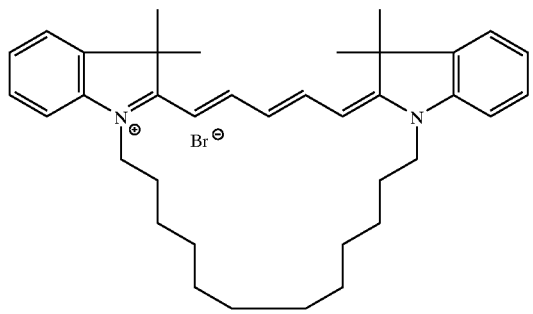

Compound 18 (66 mg, 0.10 mmol) was added and dissolved in acetic anhydride (3 mL). To that solution, sodium acetate (500 mg) and malonaldehyde phenyl imine (28 mg, 0.10 mmol) were added, respectively. The mixture was then heated to 135° C. for 2 hours. The reaction was monitored spectrophotometrically by the appearance of a peak at 656 nm (CH$_2$Cl$_2$). The reaction mixture was cooled to room temperature and the crude solution was concentrated on a rotovapor. The concentrate was then loaded onto preparatory TLC plates (silica, 10% MeOH in CH$_2$Cl$_2$) to obtain the desired purified product 19. Yield 50 mg (81%). R$_f$=0.3 (5% MeOH in CH$_2$Cl$_2$). δ$_{max}$ (CH$_2$Cl$_2$) 656; δ$_{em}$ (CH$_2$Cl$_2$) 674 nm. $^1$H NMR (CDCl$_3$, 360 MHz) δ 8.20 (m, 2H), 7.65 (d, 2H, J=7.4Hz), 7.15–7.38 (m, 5H), 7.05 (dd, 2H, J=1.2Hz, 7.4Hz), 6.22 (m,2H), 4.04 (bt, 4H), 1.86 (m, 4H), 1.20–1.50 (m, 28H). MS (FAB, NBA), calculated for C$_{37}$H$_{49}$N$_2$Br, 601; found 521 (M-Br, 15%).

Example 12

Synthesis of Dodecanyl Bridged Indoleninium Squaraine Dye (20)

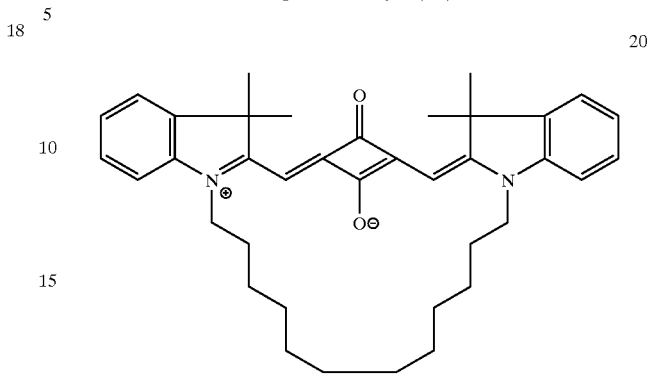

Compound 18 (66 mg, 0.10 mmol) was added and dissolved in 1:1 (v/v) n-butanol and toluene (3 mL). To that solution, 3,4-hydroxy-3-cyclobuten-1,2-dione (11 mg, 0.10 mmol) was added. The solution was heated to 135° C. for 2 hours. The solution was then cooled to room temperature and 5 mL of water was added. The solution was then extracted three times with 15 mL of dichloromethane. The extract was dried with sodium sulfate, filtered using vacuum filtration, and concentrated on a rotovapor. The crude concentrate was purified using preparative TLC (2% MeOH in CH$_2$Cl$_2$) to obtain the desired purified product 20. Yield 30 mg (50%). Rf=0.35 (5% MeOH in CH$_2$Cl$_2$. δ$_{max}$ (CH$_2$Cl$_2$) 648 nm: $^1$H NMR (CDCl$_3$, 300 MHz) δ 7.32 (m, 4H, 7.13 (bt, 2H), 6.96 (bt, 2H),

Example 13

Synthesis of Dodecanyl Bridged Indoleninium Heptamethine Cyanine Dye (21)

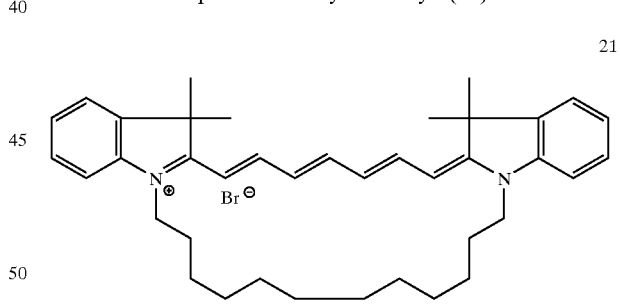

Compound 18 (400 mg, 0.61 mmol) was dissolved in acetic anhydride (4 mL). To that solution, sodium acetate (690 mg) and glutaconic aldehyde phenyl imine (195 mg, 0.68 mmol) were added, respectively. The reaction mixture was heated to 135° C. for 2 hours. The mixture was then cooled to room temperature and the crude solution was concentrated on a rotovapor. The concentrate was then loaded onto preparatory TLC plates (10% methanol/dichloromethane) to obtain the desired purified product 21. Yield 190 mg (49%). Rf=0.6 (5% MeOH in CH$_2$Cl$_2$). δ$_{max}$ (CH$_2$Cl$_2$) 760 nm; δ$_{em}$ (CH$_2$Cl$_2$) 790 nm $^1$H NMR (CDCl$_3$, 360 MHz) δ 7.78 (m, 2H), 7.45–7.65 (m, 4H), 7.47 (m, 3H), 7.00–7.21 (m, 4H), 6.24 (bd, 2H). MS(FAB, NBA), calculated for C$_{39}$H$_{51}$N$_2$Br 627; found 547 (M-Br, 60%).

Example 14

Synthesis of C12 Linked 2,3,3-trimethyl-benzindolenine (22)

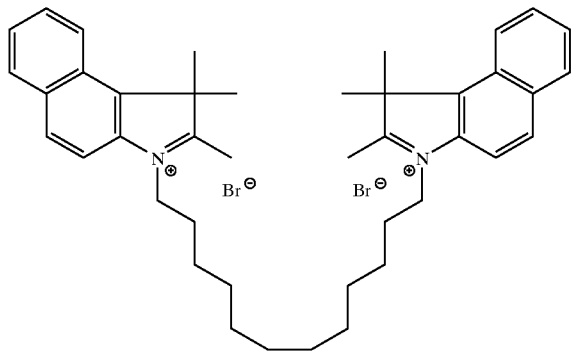

Dibromododecane (1.9 g, 5.9 mmol) was dissolved in o-dichlorobenzene (5 mL). 2,3,3-trimethylbenzindolenine (5.0 g, 23.8 mmol) was added and the solution was heated to reflux for 24 hours. The reaction mixture was cooled to room temperature and the crude solution was loaded onto a silica gel column and chromatographed (0 to 20% MeOH in $CH_2Cl_2$) to obtain the desired product 22. Yield 3.0 g (66%). Rf- 0.6 (5% MeOH in $CH_2Cl_2$). $^1$H-NMR ($CDCl_3$, 360 MHz) δ 8.06 (d, 2H), 8.02 (d, 2H) 7.97 (d, 2H), 7.79 (d, 2H), 7.66 (dd, 2H), 7.60 (dd, 2H), 4.78 (t, 4H), 3.17 (s, 6H), 1.95 (m, 4H), 1.80 (s, 12H), 1.46 (m, 4H), 1.40 (m, 4H), 1.19 (m, 8H).

Example 15

Synthesis of Dodecanyl Bridged Benzindoleninium Pentamethine Cyanine dye (23)

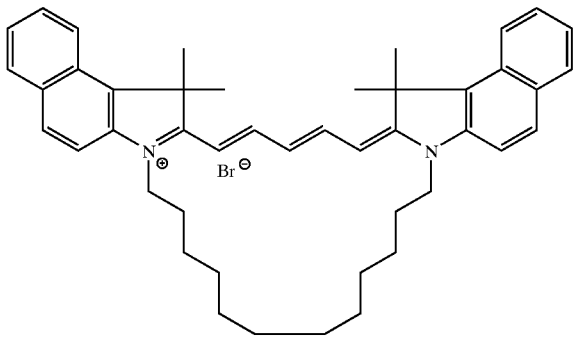

Compound 22 (415 mg, 0.55 mmol) was dissolved in acetic anhydride (3 mL). To that solution, sodium acetate (500 mg) and malonaldehyde phenyl imine (142 mg, 0.55 mmol) were added respectively. The reaction mixture was heated to 135° C. for 2 hours. The reaction mixture was then cooled to room temperature and the crude solution was concentrated on a rotovapor. The concentrate was then loaded onto preparatory TLC plates (10% methanol/dichloromethane) to obtain the desired purified product 23. Yield 210 mg (52%). Rf=0.6 (5% methanol/dichloromethane). $δ_{max}$ ($CH_2Cl_2$) 696 nm; $δ_{em}$ ($CH_2Cl_2$) 716 nm. $^1$H δ 8.17 (m, 2H), 7.72 NMR ($CDCl_3$, 300 MHz) δ 8.17 (m, 2H), 7.78 (m, 2H), 7.72 (t, 1H, J=14Hz), 7.53), 7.53 (d, 4H, J=8.4Hz), 7.42 (m, 2H), 7.28 (d, 2H, J=8.4Hz), 7.14 (t, 2H, J=7.6Hz), 6.24 (d, ~2H, J=14Hz).

Example 16

Synthesis of Dodecanyl Bridged Benzindoleninium Squaraine Dye (24)

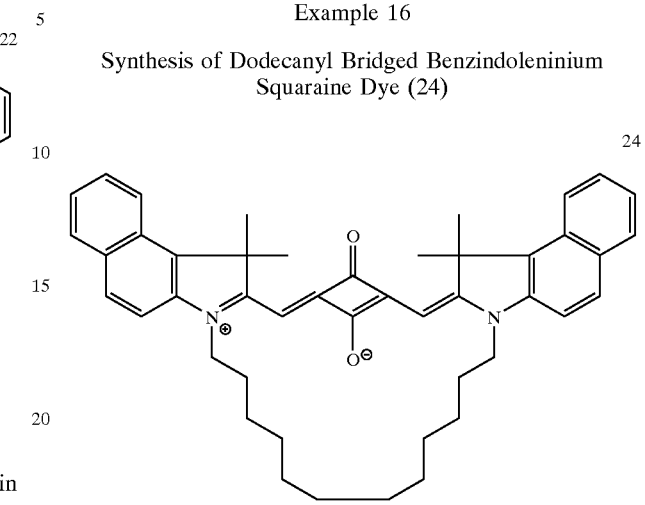

Compound 22 (375 mg, 0.49 mmol) was added and dissolved in 1:1 (v/v) n-butanol and toluene (3 mL). To that solution, 3,4 hydroxy-3-cyclobuten-1,2-dione (55 mg, 0.49 mmol) was added. The solution was heated to 135° C. for 2 hours and then was cooled to room temperature and 5 mL of water was added. The solution was then extracted three times with 15 mL of dichloromethane. The extract was dried with sodium sulfate, filtered using vacuum filtration, and concentrated on a rotovapor. The crude concentrate was purified using preparatory TLC (2% MeOH in $CH_2Cl_2$) to obtain the desired purified product 24. Yield 150 mg (45%). $R_f$=0.7 (5% MeOH in $CH_2Cl_2$). $δ_{max}$ ($CH_2Cl_2$) 671 nm; $δ_{em}$ ($CH_2Cl_2$) 681 nm. $^1$H NMR ($CDCl_3$, 300 MHz) δ 8.10 (d, 2H, J=8.4Hz), 7.83 (m, 4H), 7.53 (m, 2H), 7.42 (d, 2H, 8.4Hz), 7.31 (m, 2H), 6.05 (bs, 2H), 4.12 (bt, 4H), 1.88 (m, 4H), 1.17–1.62 (m,28H). MS(FAB, NBA) calculated for $C_{46}H_{50}N_2O_2$ 662; found 663 (M+H$^+$, 45%).

Example 17

Synthesis of Dodecanyl Bridged Benzindoleninium Heptamethine Dye (25)

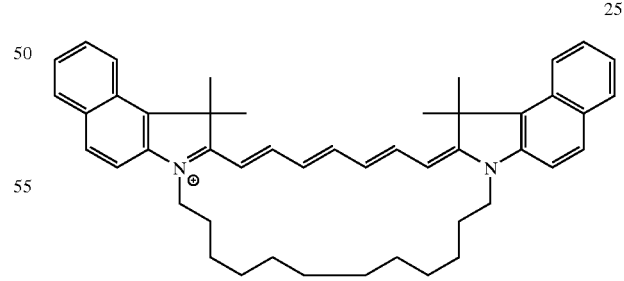

Compound 22 (256 mg, 0.34 mmol) was added and dissolved in acetic anhydride (4 mL). To that solution, sodium acetate (600 mg) and glutaconic aldehyde phenyl imine (95 mg, 0.34 mmol) were added respectively. The reaction mixture was heated to 135° C. for 2 hours. The mixture was cooled to room temperature and the crude solution was concentrated on a rotovapor. The concentrate was then loaded onto preparatory TLC plates (10% methanol/dichloromethane) to obtain the desired purified product 25. Yield 120 mg (50%). Rf=0.6 (5% MeOH in $CH_2Cl_2$). $\delta_{max}$ ($CH_2Cl_2$) 800 nm; $\delta_{em}$ ($CH_2Cl_2$) 820 nm. $^1$H NMR (CDCl$_3$, 300 MHz) δ 8.10 (m, 2H), 7.80–7.92 (m, 6H), 7.24–7.60 (m, 7H), 6.60 (m, 2H), 6.21 (m, 2H), 4.10 (bt, 4H), 1.87 (m, 4H), 1.15–1.48 (m, 28H).

Example 18

Synthesis of Dye (26)

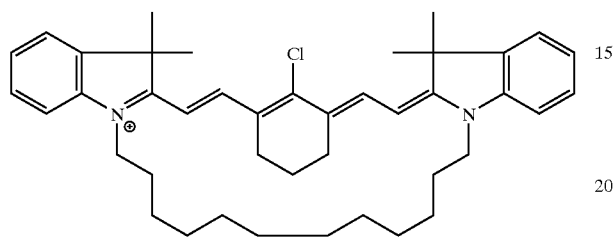

Compound 18 (79 mg, 0.12 mmol) was added and dissolved in acetic anhydride (4 mL). To that solution, sodium acetate (600 mg) and N-[(3-(anilino-methylene)-2-chloro1-1cyclohexen-1-yl)-methylene]aniline monohydrochloride (45 mg, 0.12 mmol) were added respectively. The reaction mixture was heated to 135° C. for 2 hours. The mixture was cooled to room temperature and the crude solution was loaded onto a silca gel column and chromatographed (0% to 20% methanol/dichloromethane). The desired fractions were collected and concentrated to obtain the product 26. Yield 70 mg (83%). R$_f$=0.3 (10% MeOH/CH$_2$Cl$_2$).

Example 19

Synthesis of Bridged Trimethine Indolenium Cyanine Dye (27)

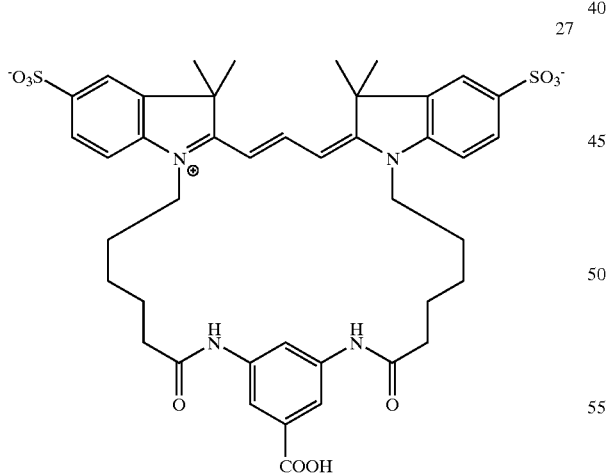

To a 5 mL vial, bridged bis(indolenium sulfonate) (48 mg, 0.058 mmol) and formamidine (12 mg, 0.058 mmol) were dissolved in 1.5 mL of acetic anhydride. Sodium acetate was added and the solution was stirred for approximately two hours. The reaction mixture was then cooled to room temperature and loaded onto a reverse phase preparative TLC plate to separate the desired product compound 27 (50% methanol/water). $\delta_{max}$ 563 nm.

Example 20

Synthesis of Bridged Thiosquarylium Dye (28)

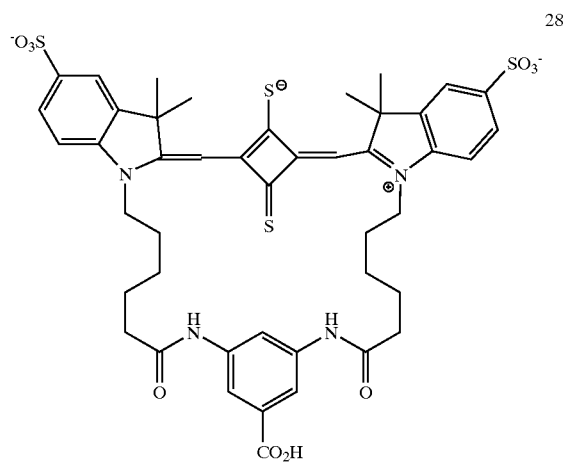

To a 20 mL reaction vial, bridged squarylium dye 15 (10 mg, 0.012 mmol) was dissolved in 4 mL HMPA. Phosphorus pentasulfide (100 mg, 0.22 mmol) was then added and the solution was heated to 130° C. for two hours. The solution was then cooled to room temperature and the product (28) confirmed by absorbance spectra. $\delta_{max}$ 649 nm.

Example 21

Preparation of Non-sulfonated Bridged bis(2,3-trimethyl1 benzindoleninium) (29)

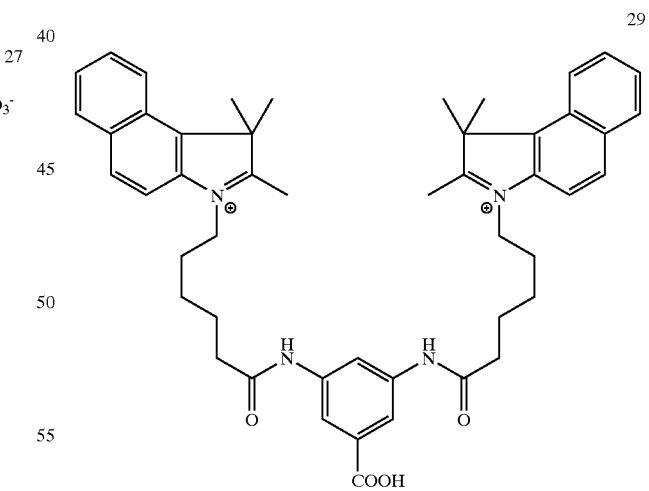

To a 50 mL round bottom flask the bridging precursor (10) (1.0 g, 1.97 mmol) was dissolved in 10 mL of o-dichlorobenzene and benzindolenine (863 mg, 4.13 mmol) was added. The reaction mixture was heated to 140° C. and stirred for 24 hours. The mixture was then cooled to room temperature and the solvent was decanted. The solid product was triturated with ethyl acetate and vacuum dried.

Example 22

Synthesis of Bridged bis(2,3-trimethyl Benzindolenium Sulfonate) (30)

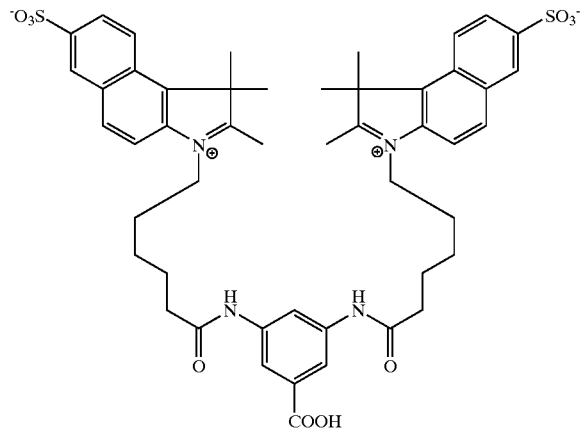

To a 10 mL round bottom flask non-sulfonated bridged benzindolenium (29) (0.5 g) was added and dissolved in sulfuric acid. The reaction mixture was heated to 180° C. and stirred for 4 hours. The mixture was then placed in a refrigerator overnight to cool. The material was then poured into a large erylenmeyer flask in an ice bath. The solution was then neutralized with 6 M NaOH. Once neutralized, the solution was concentrated and the resulting material was dissolved in methanol. The precipitated sodium sulfate was then filtered out. The filtering process was repeated once. The desired product in methanol was then concentrated and vacuum dried.

Example 23

Preparation of Hexanoic Acid Linked 2,3-trimethl Benindolenium Sulfonate (31)

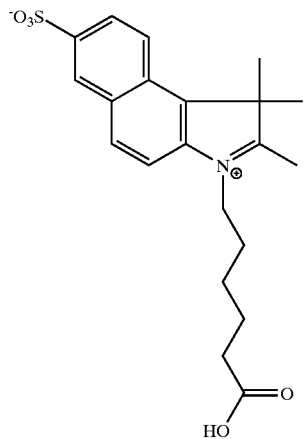

To a 250 mL round bottom flask benindolenine sulfonate (6 g, 21.0 mmol) was added and dissolved in 30 mL of o-dichlorobenzene. Diisopropylethylamine (0.3 mL, 2.1 mmol) was added and the mixture was stirred for a short period after which bromohexanoic acid (4.5 g, 23.1 mmol) was added and the mixture was heated to reflux and stirred for 24 hours. The solution was then allowed to cool to room temperature and ethyl acetate was added and the mixture was stirred for 2 hours. The product (31) precipitated out, the remaining solvent was decanted and the solid material was vacuum dried.

Example 24

Synthesis of Bridged bis(2,3-trimethyl Benzindolenium Sulfonate (30)

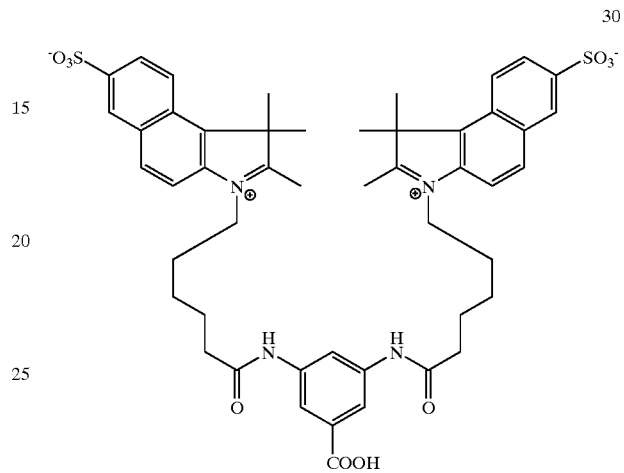

To a 250 mL round bottom flask the bridge precursor (31) (2 g, 4.9 mmol) was added and dissolved in 30 mL of methylene chloride. Dicyclohexylcarbodiimide (1.0 g, 4.9 mmol) was added and the solution was stirred for a short period. Diaminobenzoic acid (440 mg, 2.9 mmol) was then added and the mixture was stirred for 24 hours. The solution was then concentrated and the resulting product was chromatographed using reverse phase silica (0 to 100% methanol/water). The desired fractions were collected and concentrated to yield product (30).

Example 25

Synthesis of Bridged bis(2,3-trimethylbenzindolenium sulfonate) Dye (32)

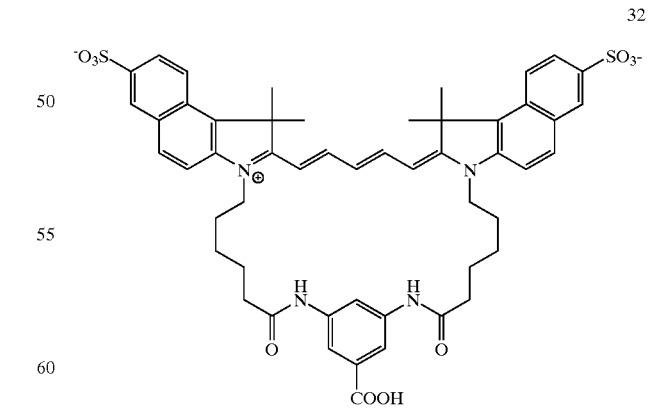

Figure 8A:
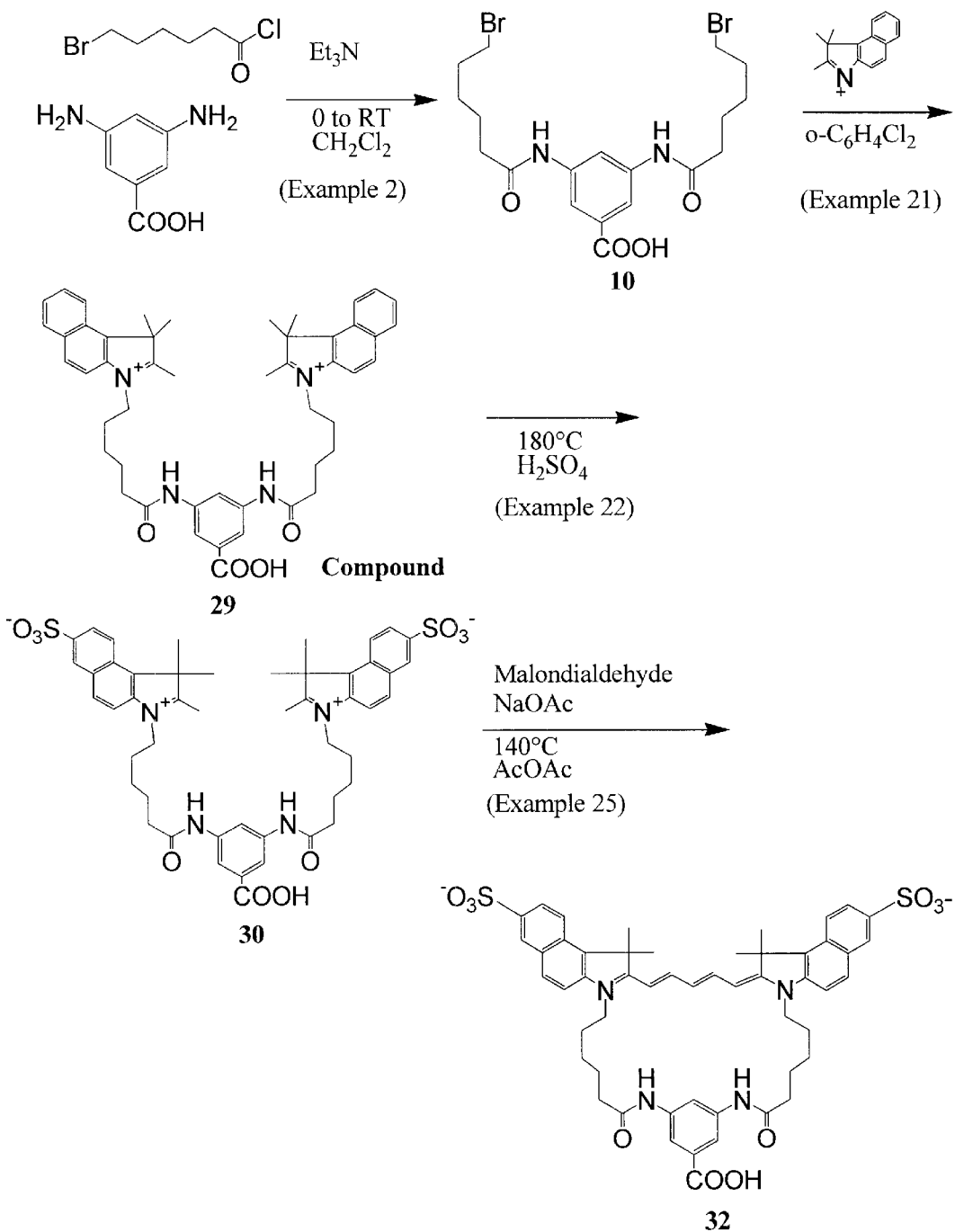
FIGS. 8A and 8B illustrate two methods for the synthesis of dye 32 (Example 25).
Figure 8B:
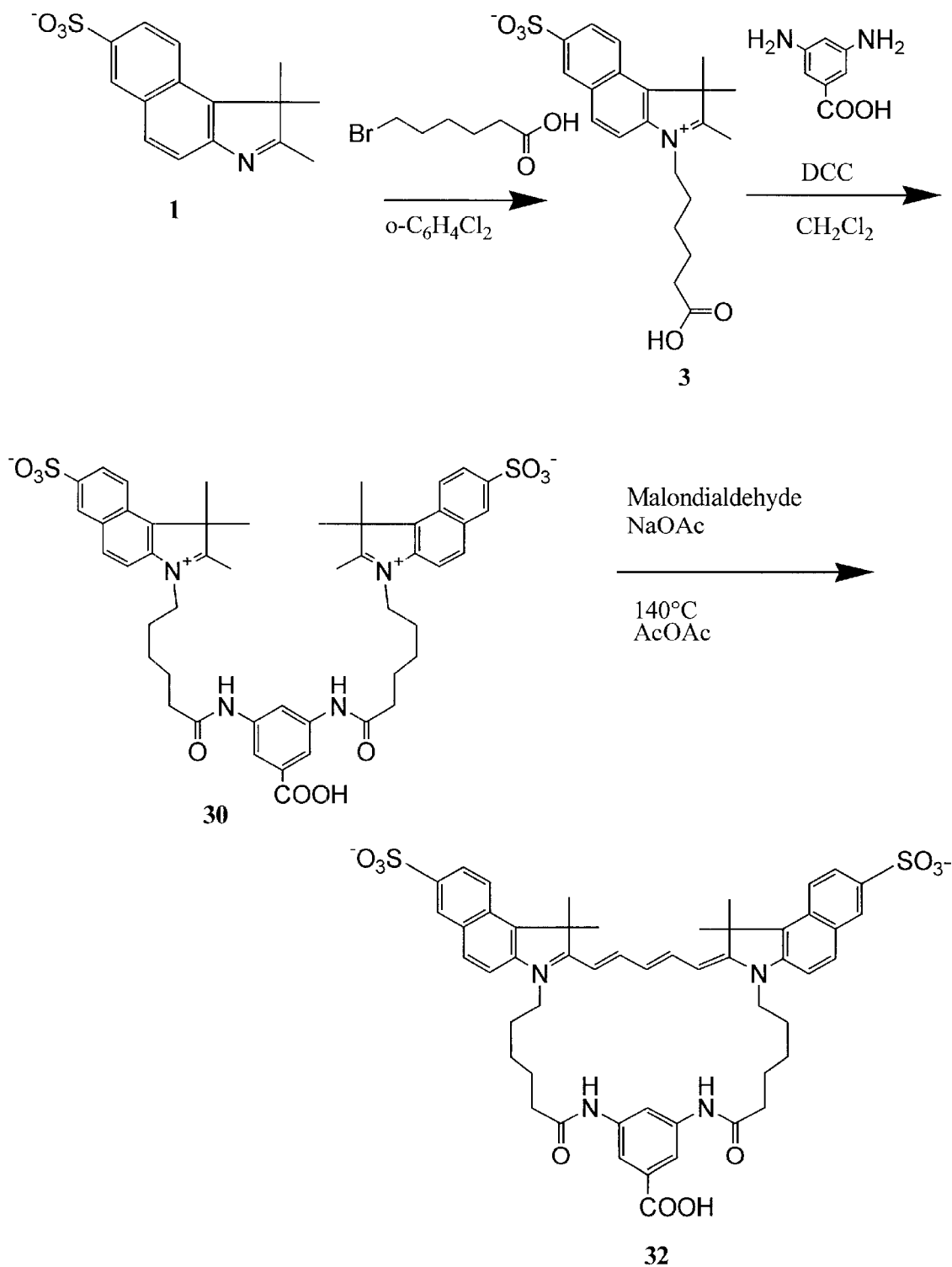

To a 25 mL round bottom flask starting bridged benindolenium sulfonate (30) (435 mg, 0.47 mmol), malondialdehyde (121 mg, 0.470 mmol) and 350 mg of sodium acetate were added and dissolved in 4 mL of acetic anhydride respectively. The reaction mixture was heated to reflux and stirred for approximately 1 hour. The mixture was then cooled to room temperature and concentrated. The concentrated material was chromatographed on reverse phase silica (0 to 100% methanol/water). The desired fractions were collected, concentrated, and vacuum dried to yield product 32. FIGS. 8A and 8B illustrate two methods for synthesizing compound 32.

Example 26

Preparation of Dye-NHS Ester

The dye was dissolved in anhydrous DMF or DMSO at a concentration of 50mg/mL and 2 equivalents of $Et_3N$ followed by 2 equivalents of disuccinimidyl carbonate were added and the solution stirred at 50° C. for 16 hours under argon. The reaction was cooled and the N-hydroxysuccinimide ester precipitated with ethylacetate. The dye NHS ester was washed with ethyl acetate centrifuged and the precipitate further washed with dioxane. Filtration under argon followed by drying yielded the dye NHS esters almost quantitatively.

Example 27

Conjugation of Dye to Protein

The dye is conjugated to the protein using the standard NHS ester conjugation protocol. The protein concentration is adjusted so final reaction concentration is 1 mM in 0.01M PBS. The dye is diluted in DMSO to achieve a predetermined final concentration. This is determined by titration of the dye to protein to find the concentration which results in the desired F/P. The NHS ester dye is added to the protein solution and incubated for 1 hour at room temperature in the dark. The reaction is stopped with the addition of glycine to a final concentration of 50 mM. The conjugates are purified either by size exclusion chromotaography or overnight dialysis into PBS azide. The F/P is determined and the protein concentration is determined spectophotometrically. The conjugate is tested for reactivity by titration.

Example 28

Examination of Spectral Properties of Dyes

Figure 9:
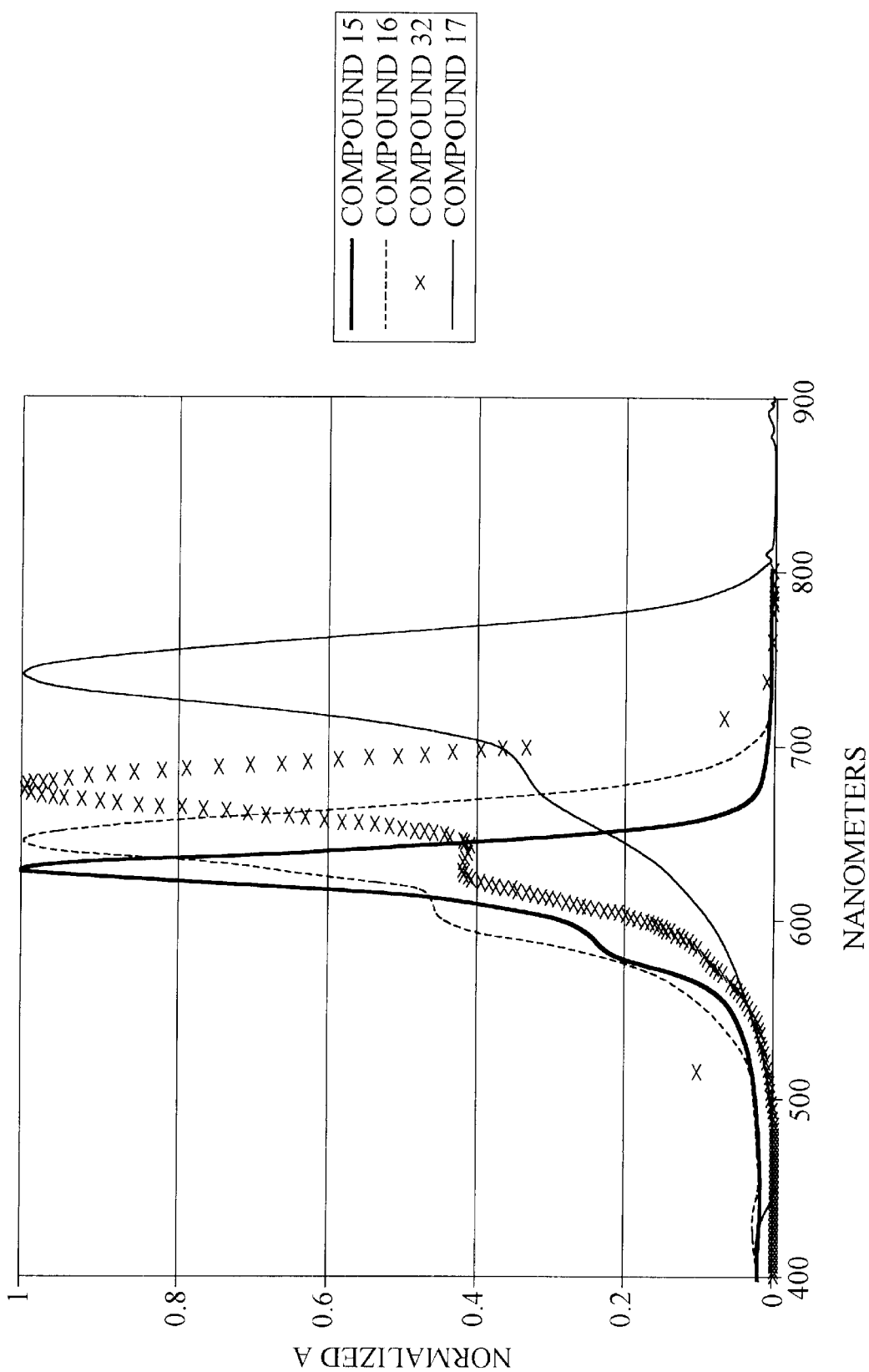
FIGS. 9 and 10 depict absorption spectra for dyes of this invention.
Figure 10:
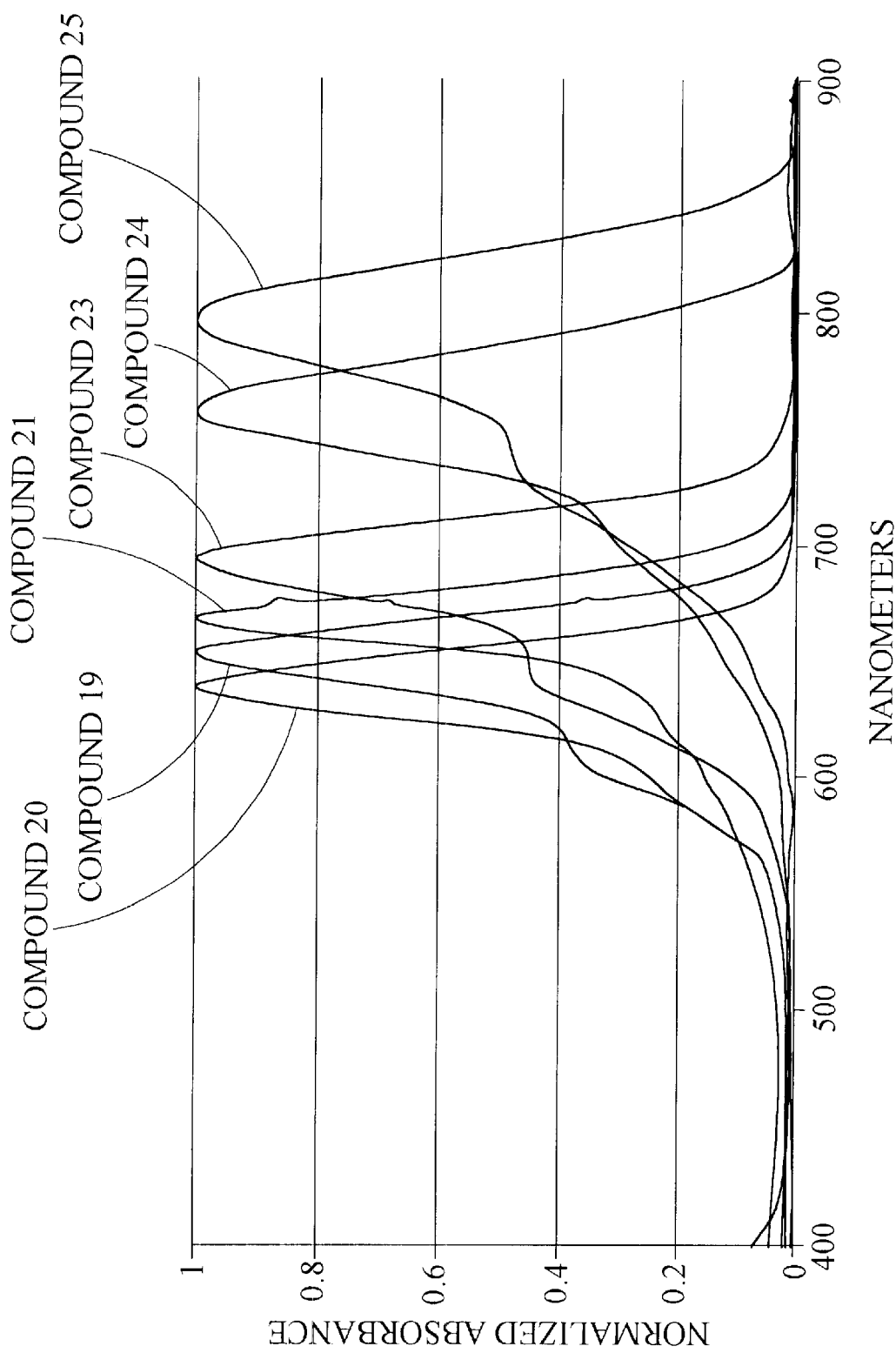
Figure 11:
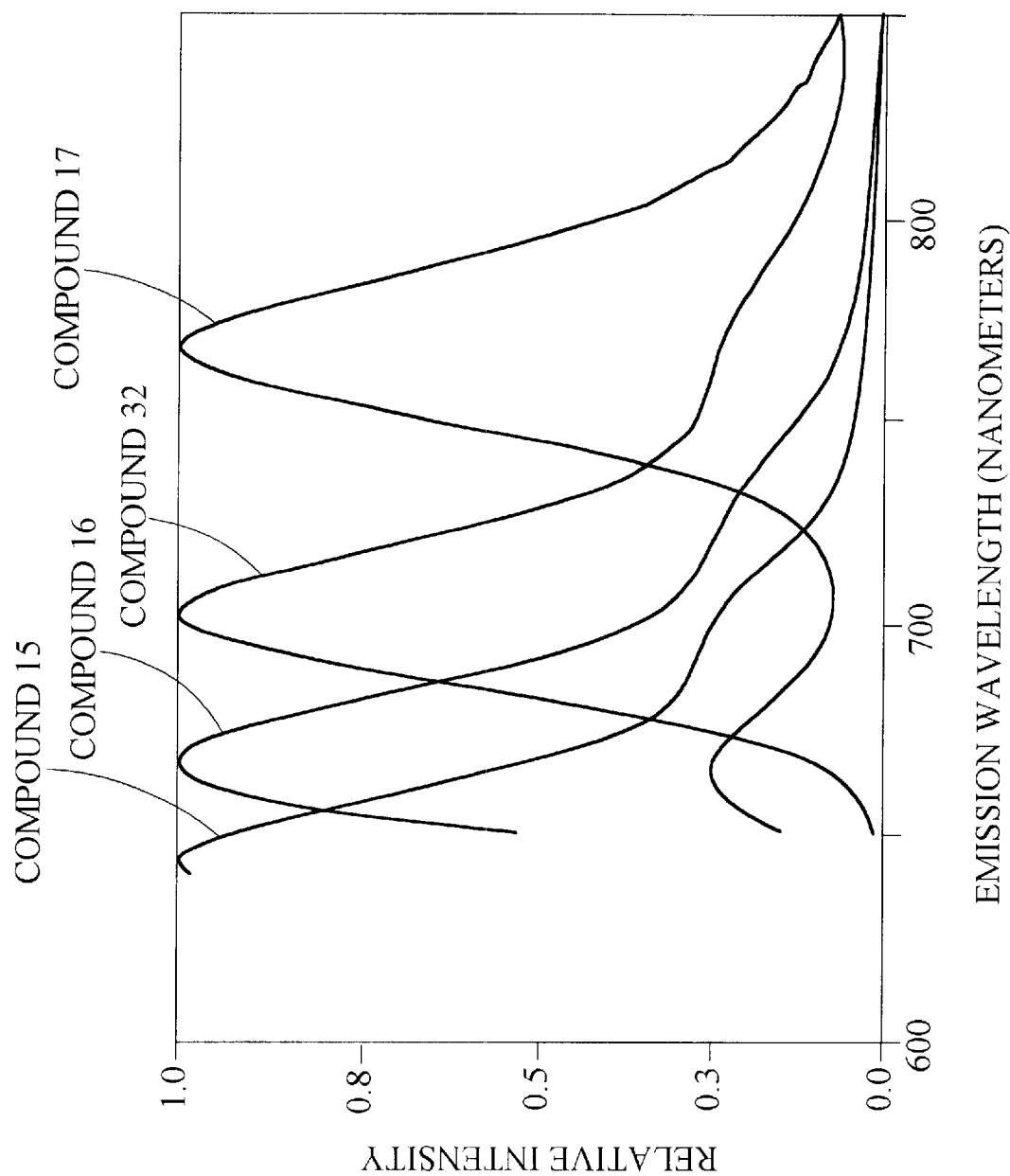
FIGS. 11 and 12 are emission spectra for dyes of this invention.
Figure 12:
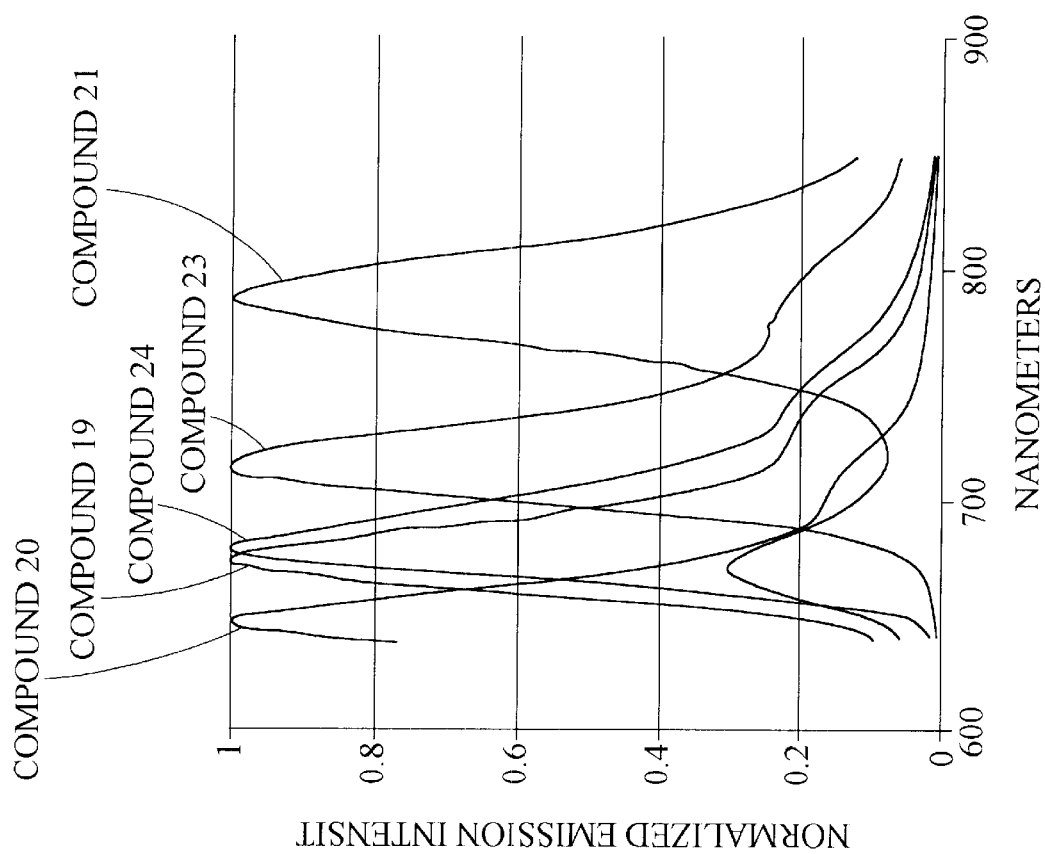

The spectral properties of the dyes of the previous Examples were measured. As shown in FIGS. 9 and 10 a range of materials were found to exhibit substantial absorbance at the 633 nm wavelength of the HeNe laser. Other materials absorbed at the 547 nm krypton laser wavelength. These materials exhibited a variety of emission wavelengths ranging from about 640 nm to about 800 nm, as shown in FIGS. 11 and 12.

What is claimed:

1. A bridged fluorescent dye having the formula:

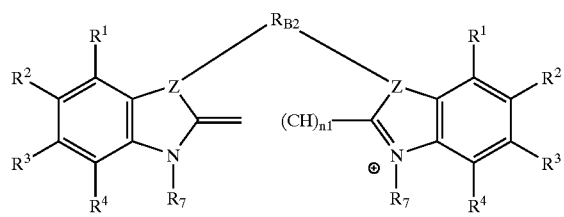

wherein:

$R_{B2}$ is a bridge of from 8 to about 30 atoms in length;

Z is O, S, Se, N, or $-CR^5R^6$;

$R^1$, $R^2$, $R^3$ and $R^4$ are each independently, hydrogen, lower alkyl, substituted lower alkyl, water solubilizing group or adjacent pairs of Rs form an aromatic structure or cycloaliphatic structure with or without substitution, and wherein at least one of $R^1$, $R^2$, $R^3$ and $R^4$ is a water solubilizing group;

$R^5$ and $R^6$ are each lower alkyls or together form a cycloalkyl;

$R^7$ is independently alkyl or alkenyl substituent; and $n_1$ is an integer from 3 to 11.

2. A bridged fluorescent dye having the formula:

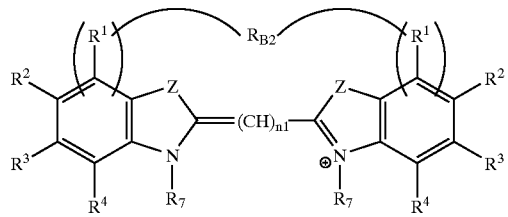

wherein:

$R_{B2}$ is a bridge of from 8 to about 30 atoms in length attached at the $R^1$ position;

Z is O, S, Se, N, or $-CR^5R^6$;

$R^1$, $R^2$, $R^3$ and $R^4$ are each independently, hydrogen, lower alkyl, substituted lower alkyl, water solubilizing group or adjacent pairs of Rs form an aromatic structure or cycloaliphatic structure with or without substitution, and wherein at least one of $R^1$, $R^2$, $R^3$ and $R^4$ is a water solubilizing group;

$R^5$ and $R^6$ are each lower alkyls or together form a cycloalkyl; and $R^7$ is independently alkyl or alkenyl substituent; and $n_1$ is an integer from 3 to 1.

3. A bridged fluorescent dye having the formula:

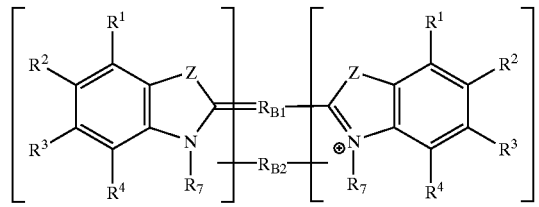

wherein $R_{B1}$ is:

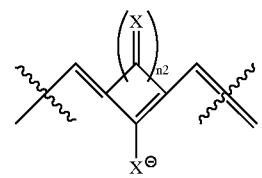

wherein $n_2$ is 1, 2, or 3;

X is selected from the group consisting of O, S and Se, such that the dye has the formula:

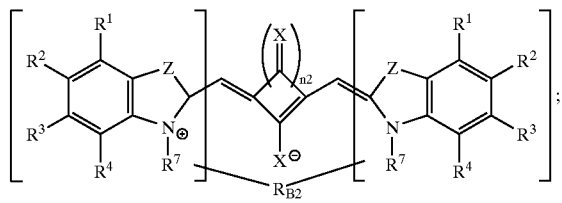

wherein $R_{B2}$ is a bridge of from 8 to about 30 atoms in length each end of which is attached at the $R^1$, N or Z positions;

Z is O, S, Se, N, or —$CR^5R^6$;

$R^1$, $R^2$, $R^3$ and $R^4$ are each independently, hydrogen, lower alkyl, substituted lower alkyl, water solubilizing group or adjacent pairs of Rs from an aromatic structure or cycloaliphatic structure with or without substitution, and wherein at least one of $R^1$, $R^2$, $R^3$ and $R^4$ is a water solubilizing group;

$R^5$ and $R^6$ are each lower alkyls or together form a cycloalkyl; and $R^7$ is independently alkyl or alkenyl substituent, or both $R^7$ groups taken together are $R_{B2}$.

4. The bridged fluorescent dye of claim 3 having the formula:

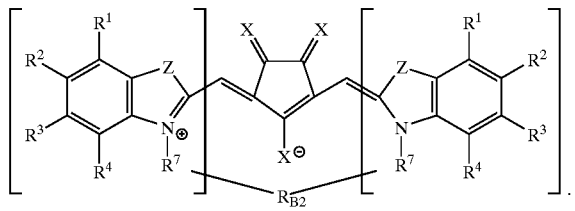

5. The bridged flourescent dye of claim 3 having a formula:

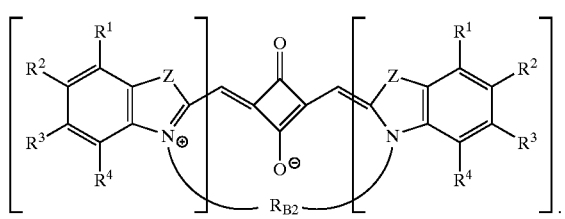

6. The bridged fluorescent dye of claim 3 having the formula:

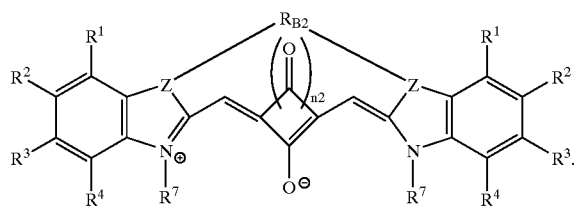

7. The bridged fluorescent dye of claim 3 having the formula:

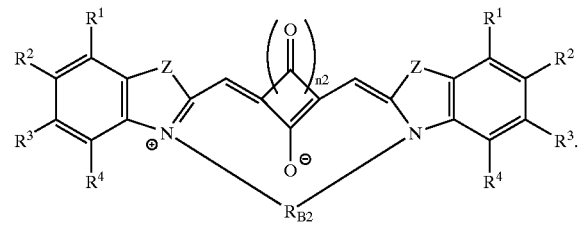

8. The bridged fluorescent dye of claim 3 having the formula:

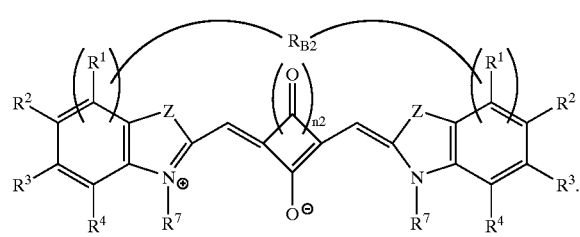

9. A bridged fluorescent dye having the formula:

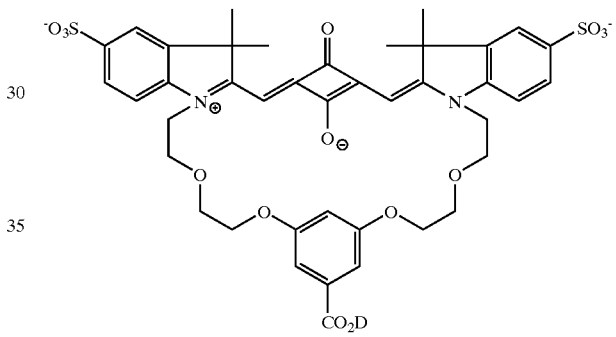

wherein D is H, an alkyl substituent, or a counterion.

10. A bridged fluorescent dye having the formula:

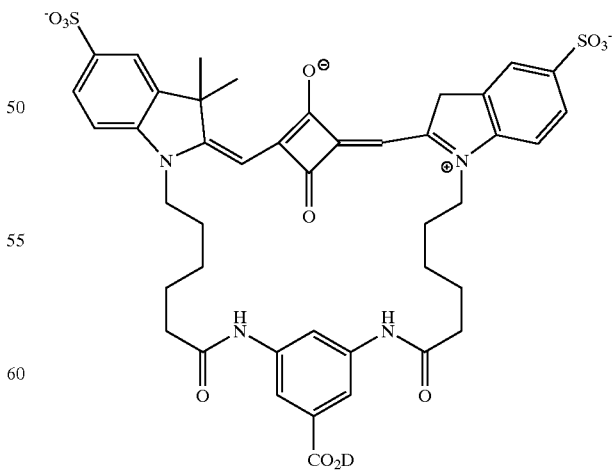

wherein D is H, an alkyl substituent, or a counterion.

11. A bridged fluorescent dye having the formula:

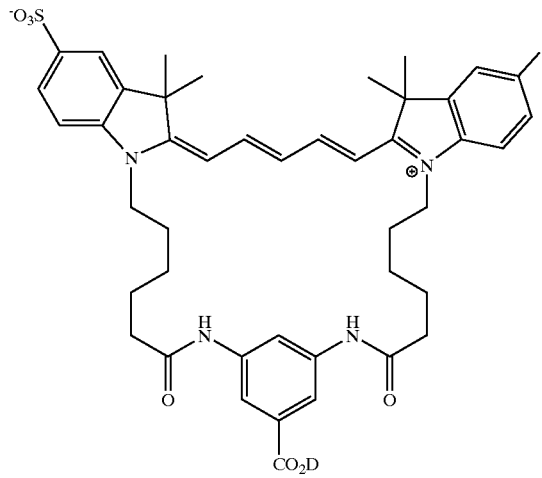

wherein D is H, an alkyl substituent, or a counterion.

12. A bridged flourescent dye having the formula:

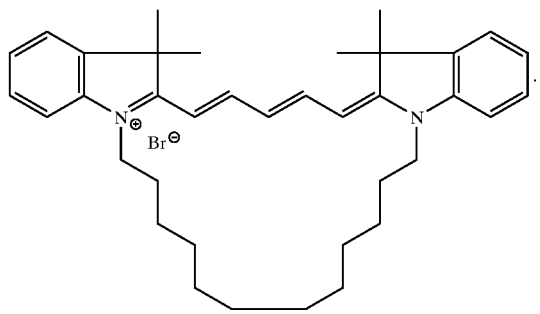

13. A bridged flourescent dye having the formula:

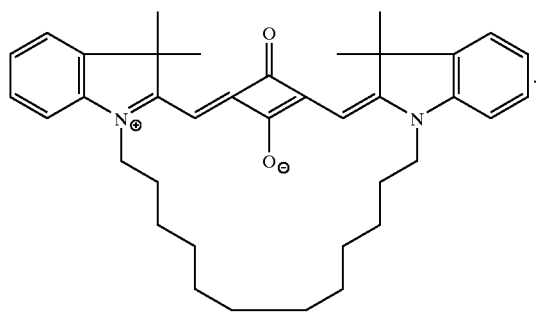

14. A bridged flourescent dye having the formula:

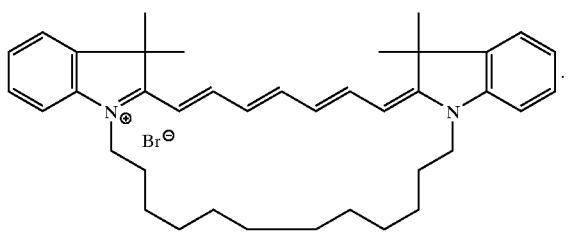

15. A bridged fluorescent dye having the formula:

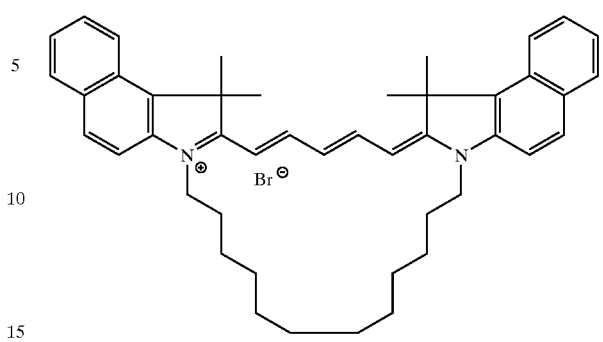

16. A bridged fluorescent dye having the formula:

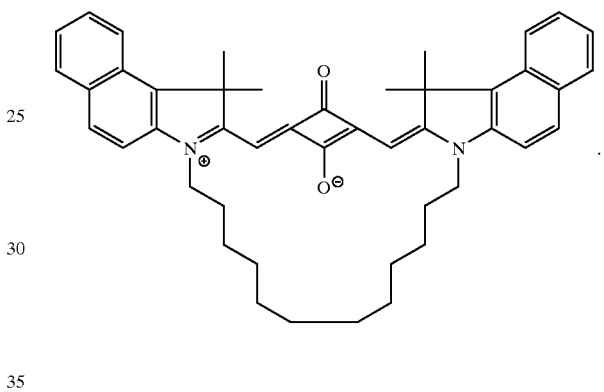

17. A bridged fluorescent dye having the formula:

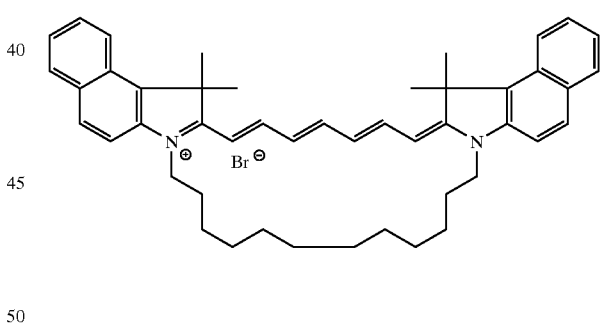

18. A bridged fluorescent dye having the formula:

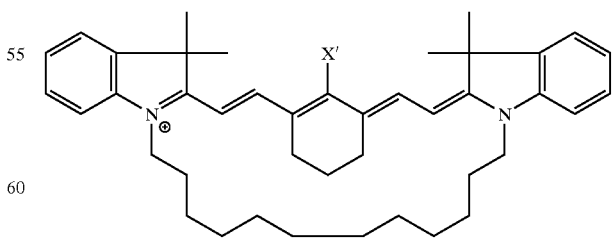

wherein X' is selected from the group consisting of a halogen, alkyl, aryl and SR, wherein R is alkyl or aryl.

19. A bridged fluorescent having the formula:
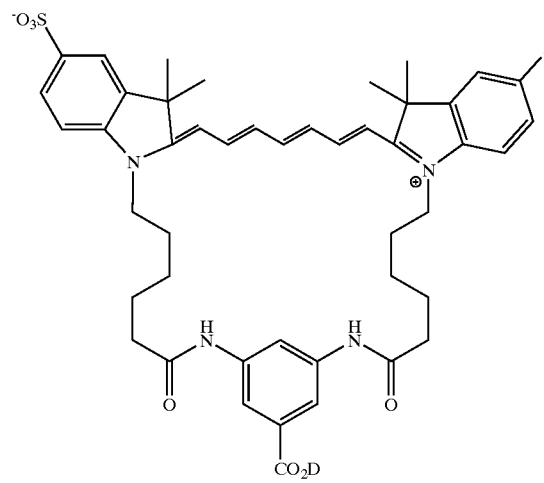
wherein D is H, an alkyl substituent, or a counterion.
20. A bridged fluorescent dye having the formula:
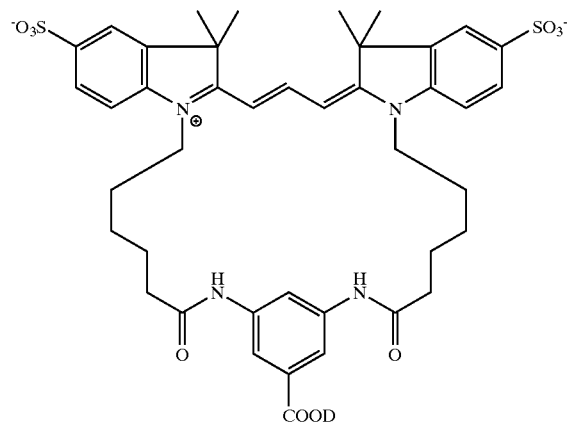
wherein D is H, an alkyl substituent, or a counterion.
* * * * *